(12) United States Patent
Herr et al.

(10) Patent No.: US 12,038,407 B2
(45) Date of Patent: Jul. 16, 2024

(54) SIMULTANEOUS DETECTION OF PROTEIN ISOFORMS AND NUCLEIC ACIDS FROM LOW STARTING CELL NUMBERS

(71) Applicant: The Regents of the University of California, Oakland, CA (US)

(72) Inventors: Amy E. Herr, Berkeley, CA (US); Lin He, Berkeley, CA (US); Andrew J. Modzelewski, Berkeley, CA (US); Elisabet Rosàs-Canyelles, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 701 days.

(21) Appl. No.: 17/327,806

(22) Filed: May 24, 2021

(65) Prior Publication Data

US 2021/0278367 A1 Sep. 9, 2021

Related U.S. Application Data

(63) Continuation of application No. PCT/US2019/066428, filed on Dec. 15, 2019.

(60) Provisional application No. 62/910,356, filed on Oct. 3, 2019, provisional application No. 62/780,183, filed on Dec. 14, 2018.

(51) Int. Cl.
| | |
|---|---|
| *G01N 27/447* | (2006.01) |
| *C08J 9/40* | (2006.01) |
| *C08K 5/1545* | (2006.01) |
| *C08L 33/26* | (2006.01) |

(52) U.S. Cl.
CPC ......... *G01N 27/44747* (2013.01); *C08J 9/40* (2013.01); *C08K 5/1545* (2013.01); *C08L 33/26* (2013.01); *C08J 2333/26* (2013.01)

(58) Field of Classification Search
None
See application file for complete search history.

(56) References Cited

U.S. PATENT DOCUMENTS

2011/0269158 A1* 11/2011 Zitzler ............ G01N 33/57415
435/7.92

FOREIGN PATENT DOCUMENTS

WO WO-0131332 A1 * 5/2001 ....... G01N 27/44717

OTHER PUBLICATIONS

Rosas-Canyelles, et al. "Single-embryo and single-blastomere immunoblotting reports protein expression heterogeneity in early-stage preimplantation embryos" BioRxiv, No. 35773, 20 pgs, Jun. 28, 2018.*

* cited by examiner

*Primary Examiner* — J. Christopher Ball
(74) *Attorney, Agent, or Firm* — Richard Aron Osman

(57) ABSTRACT

Dual nucleic acid and protein isoform measurements are performed on low starting cell numbers (e.g. equivalent to the number of blastomeres composing early embryonic development stages (morula and blastocysts)), comprising integrating fractionation polyacrylamide gel electrophoresis (fPAGE) of 10-100 cells with off-chip analysis of nucleic acids in the nuclei.

20 Claims, 19 Drawing Sheets

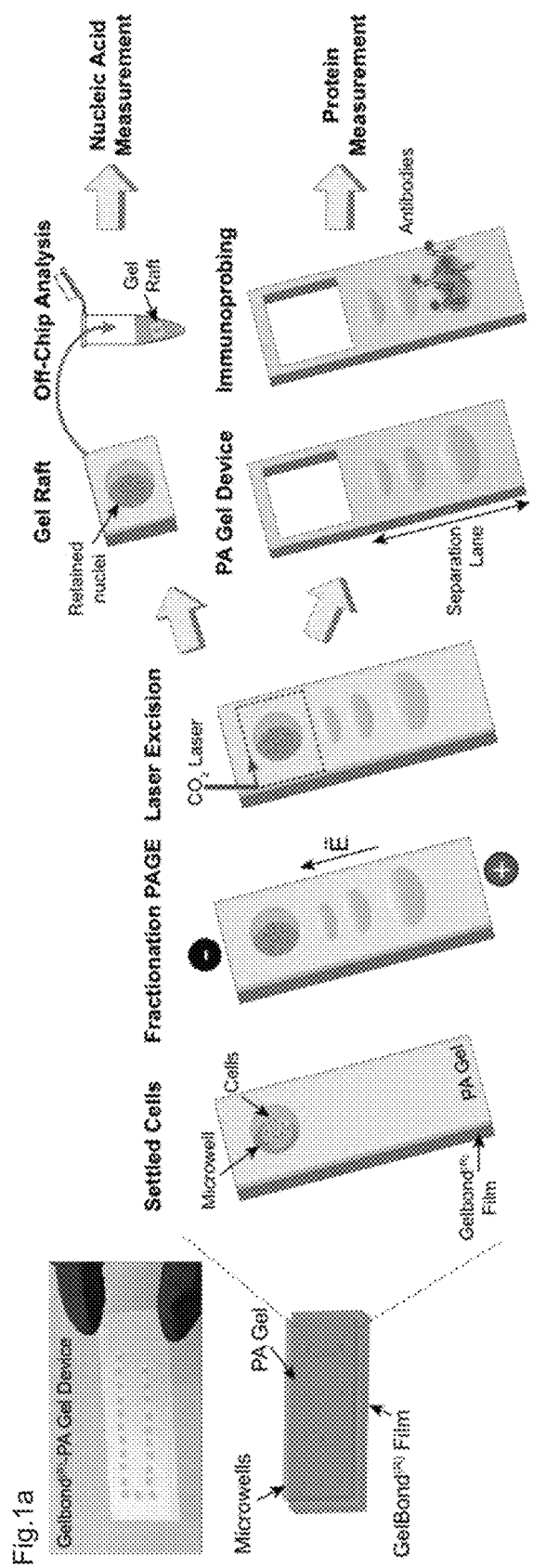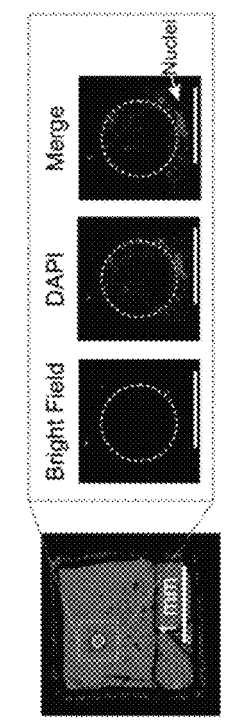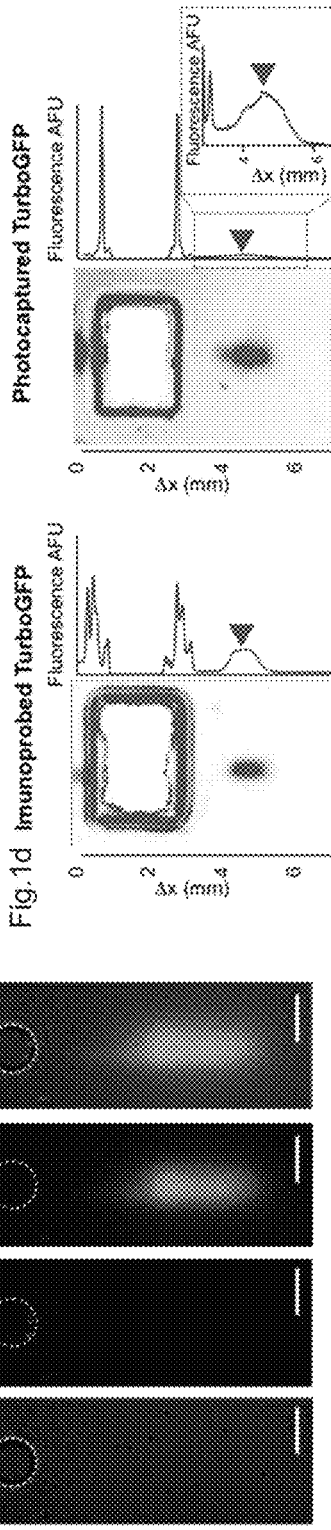

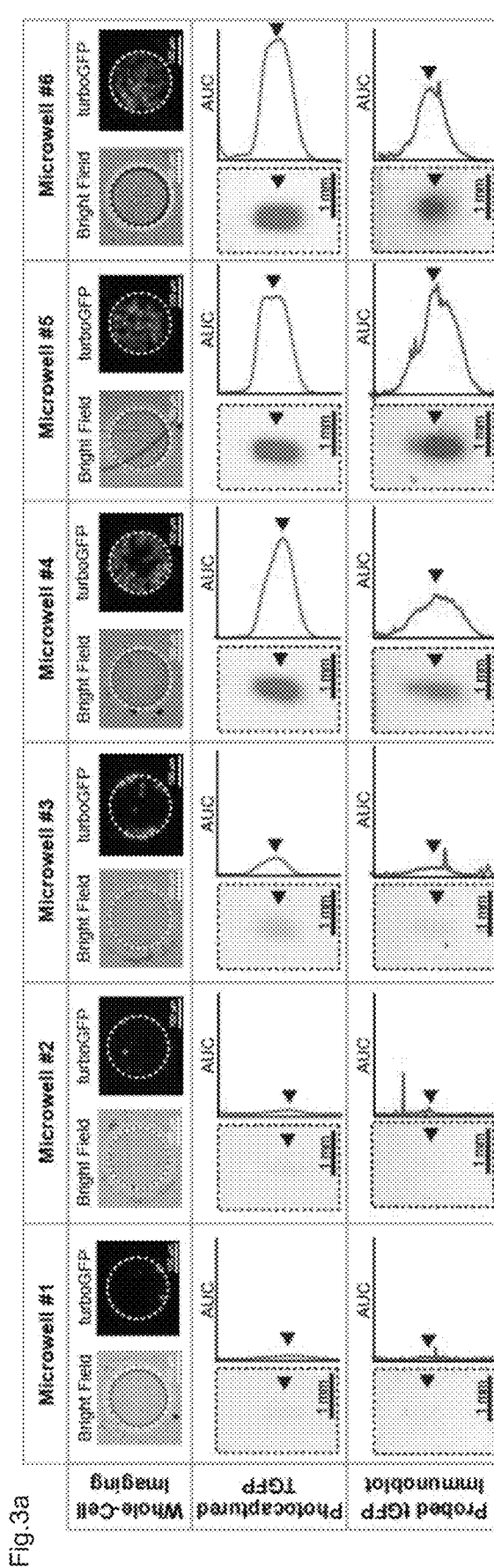
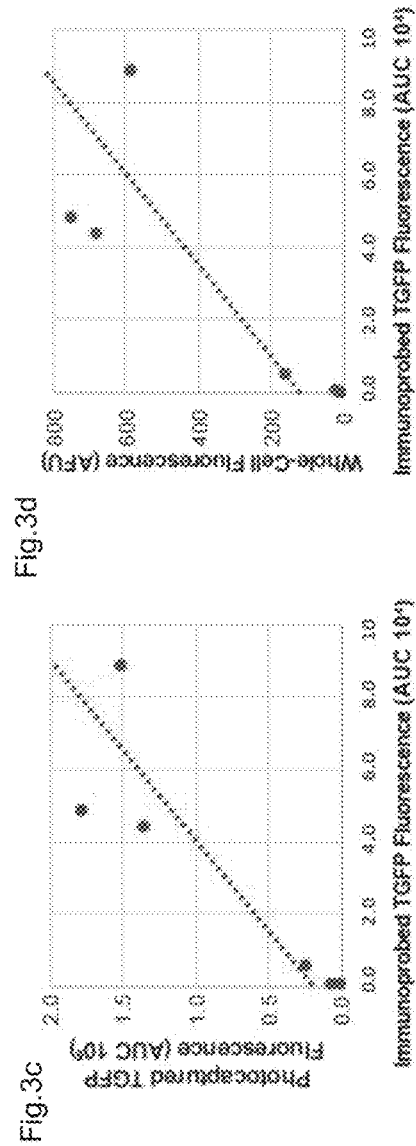
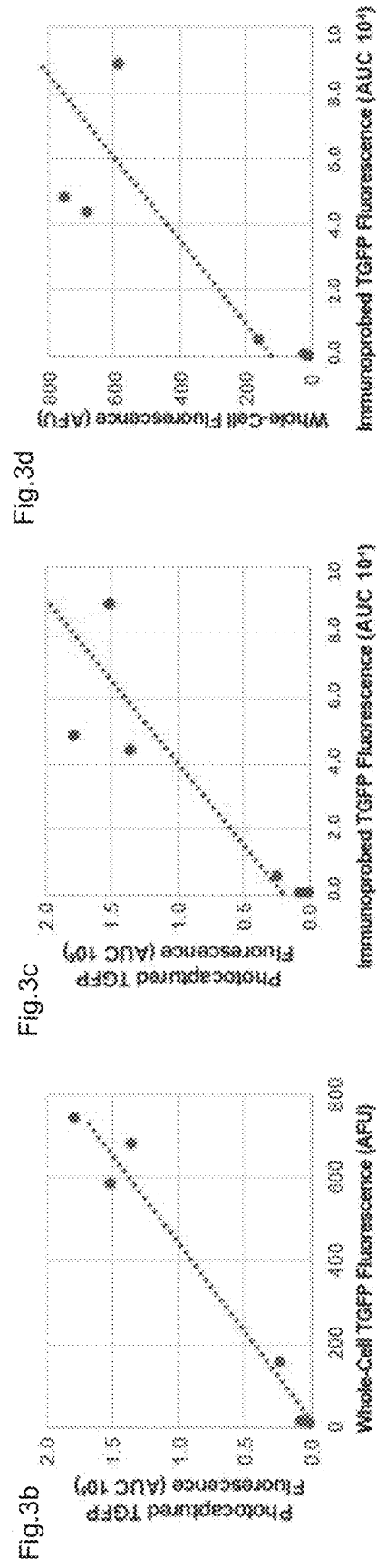
Fig. 3a
Fig. 3b
Fig. 3c
Fig. 3d

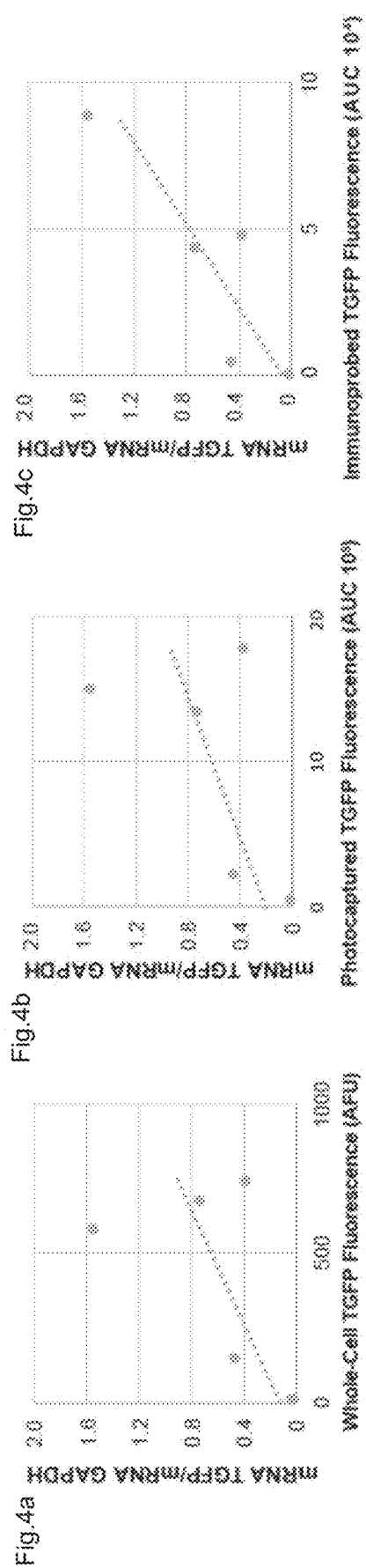

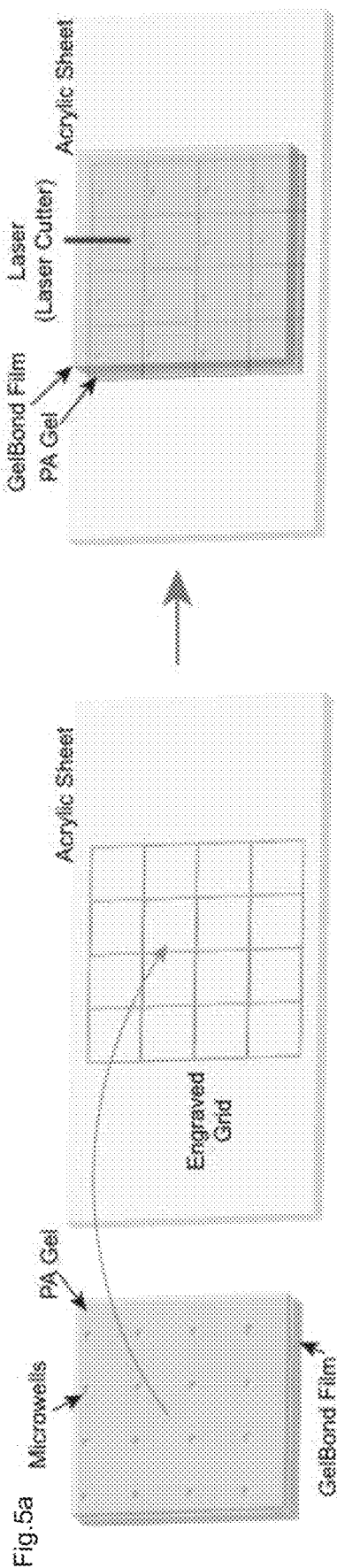
Fig.5a
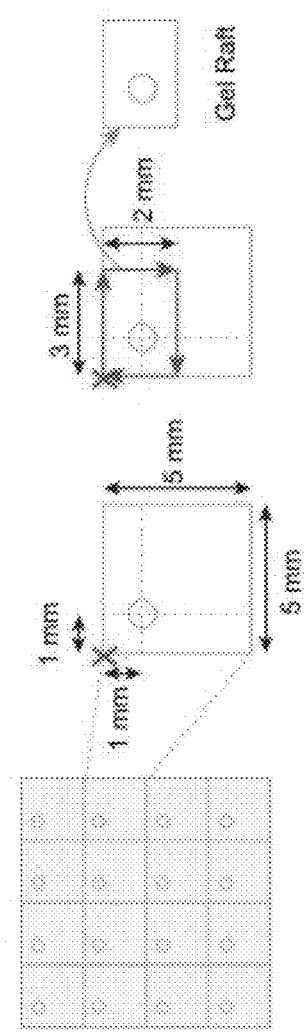
Fig.5b  Top View

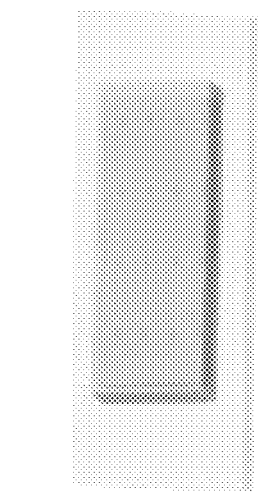
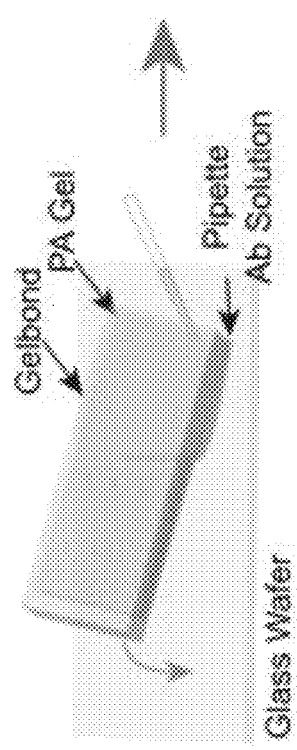
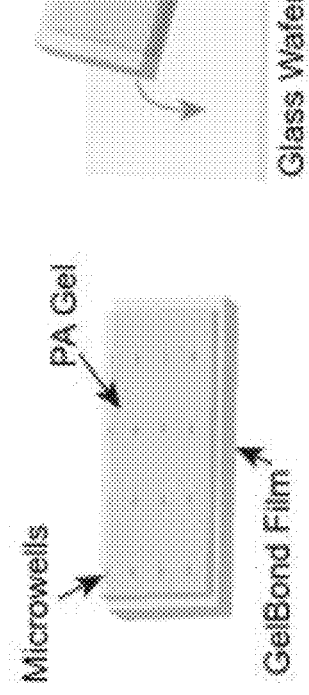
Fig. 6a
Fig. 6b
Fig. 6c
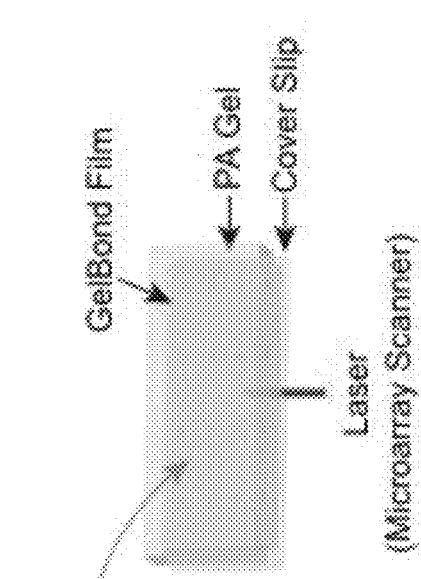
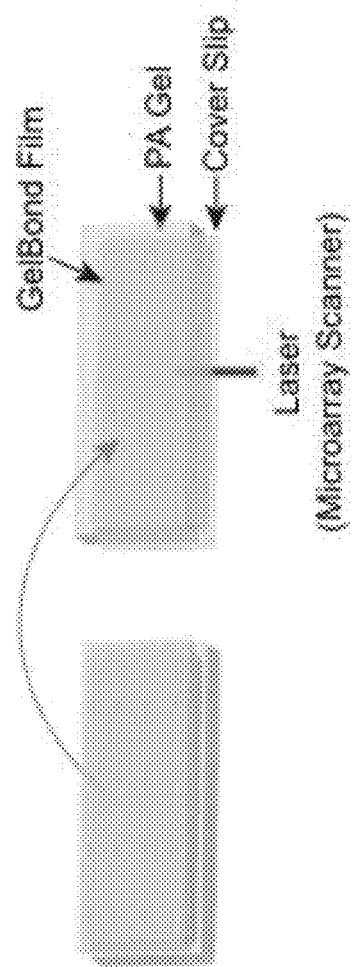
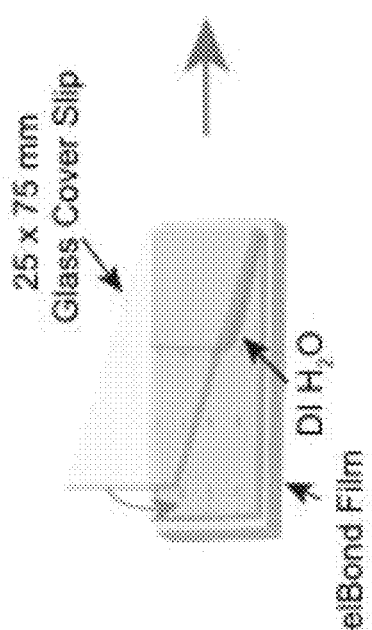

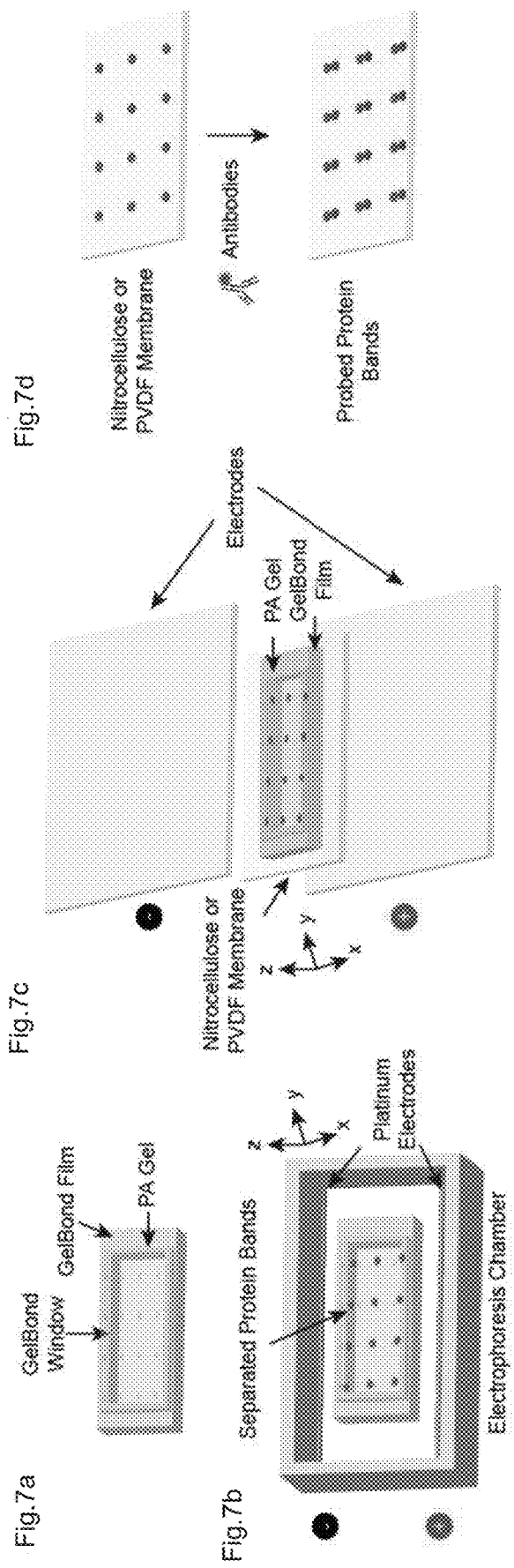

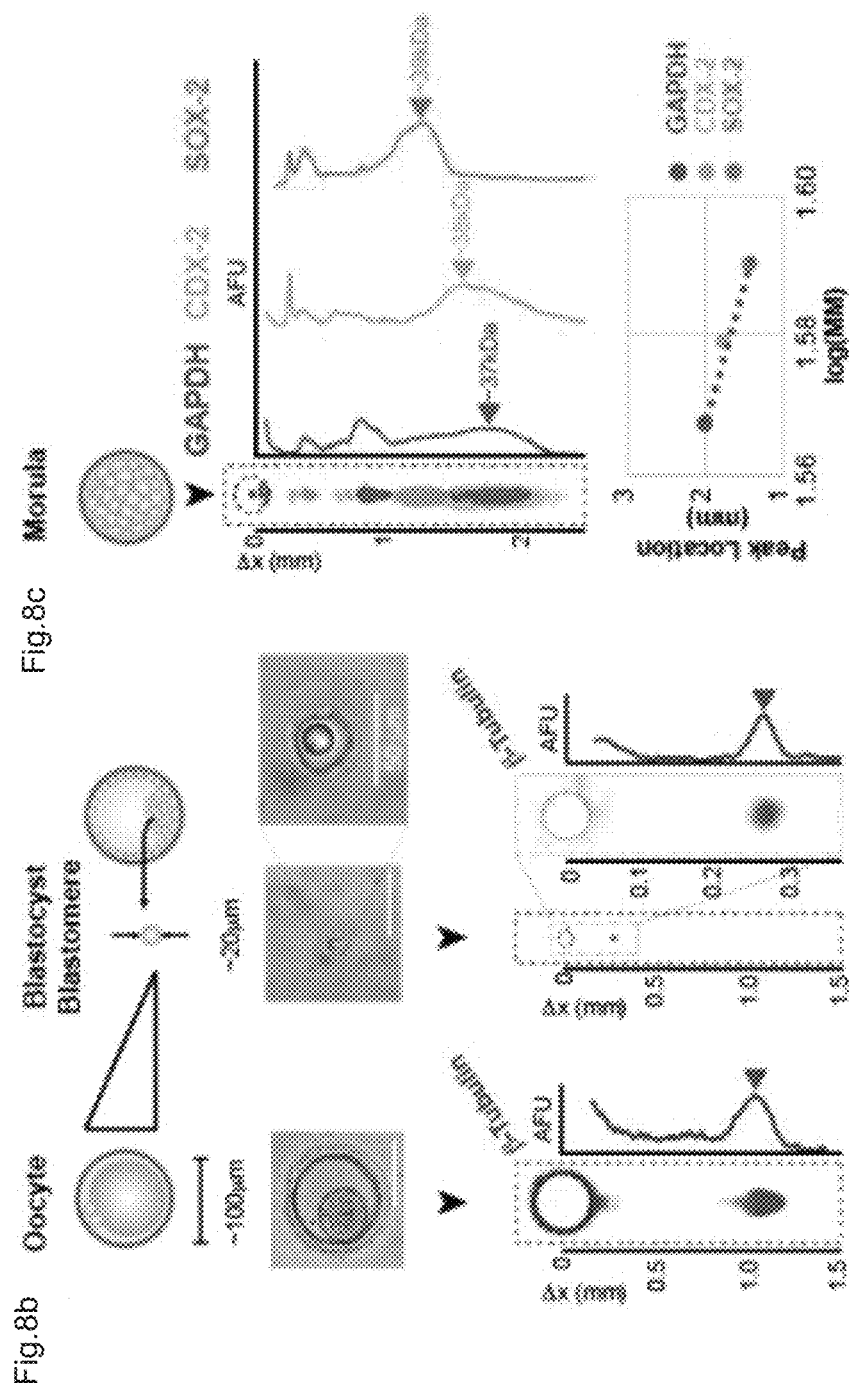

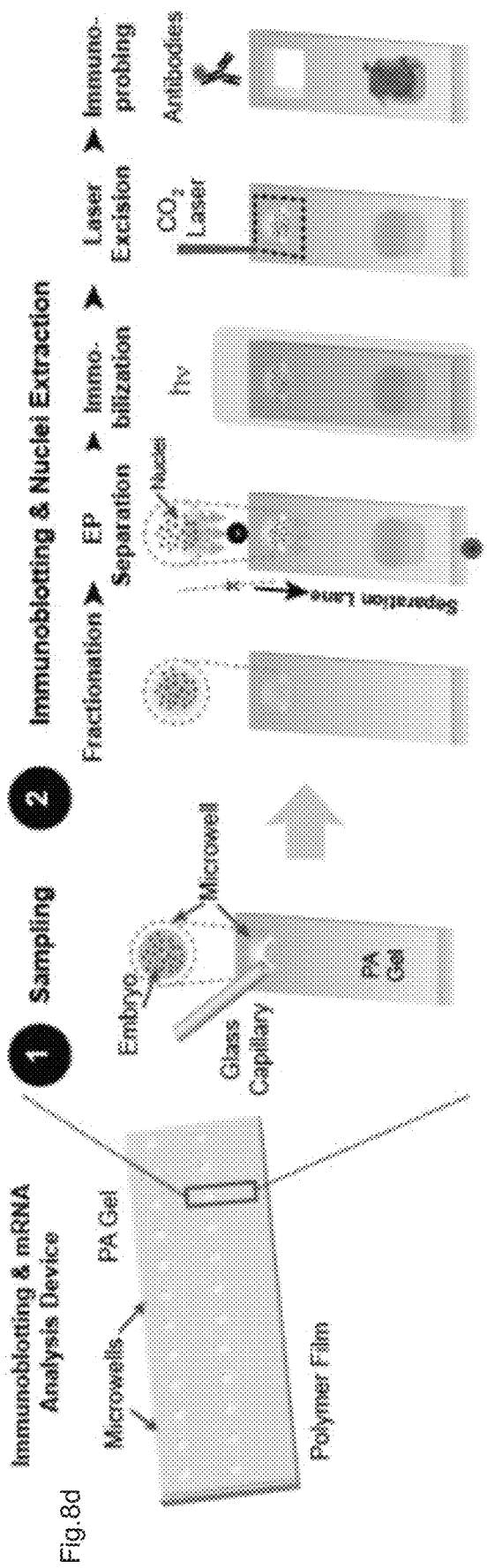
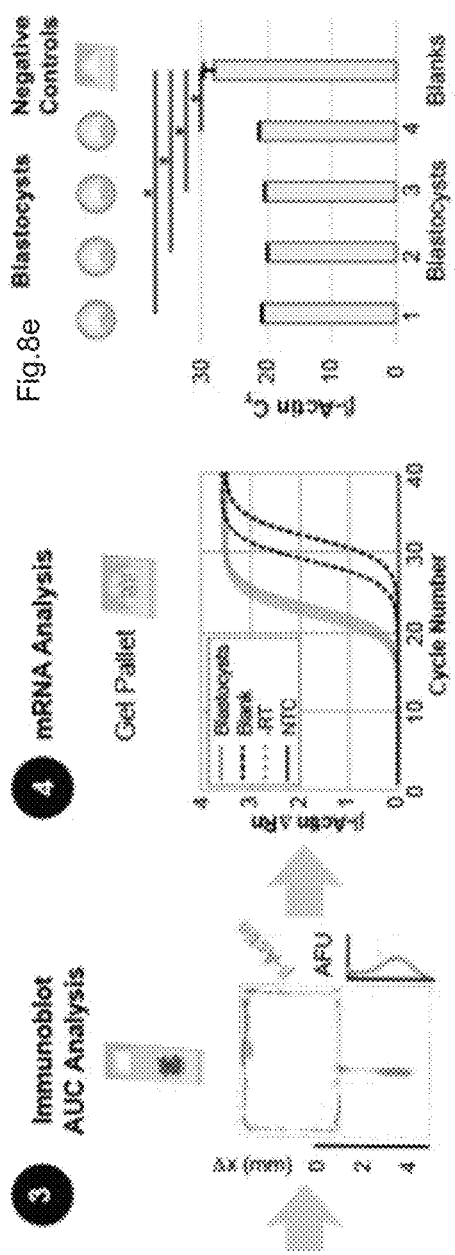
Fig. 8d
Fig. 8e

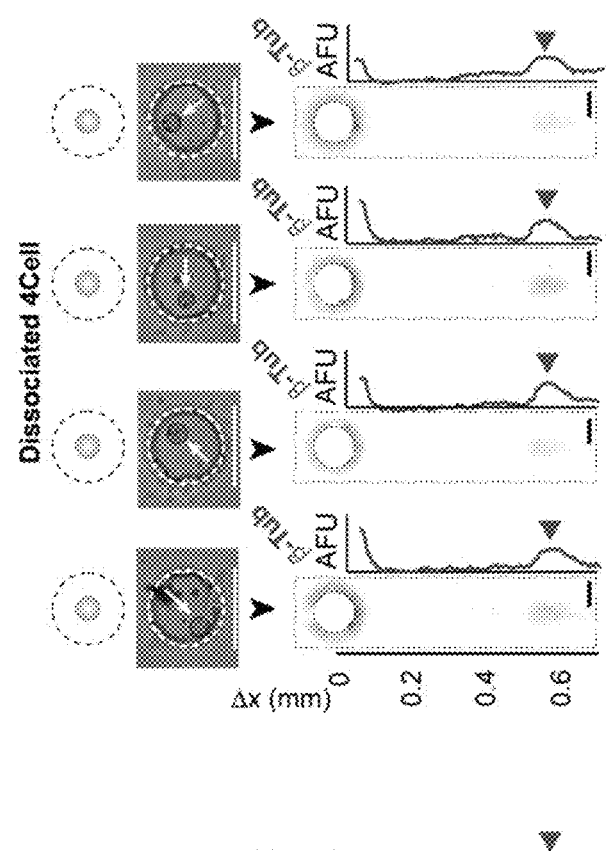
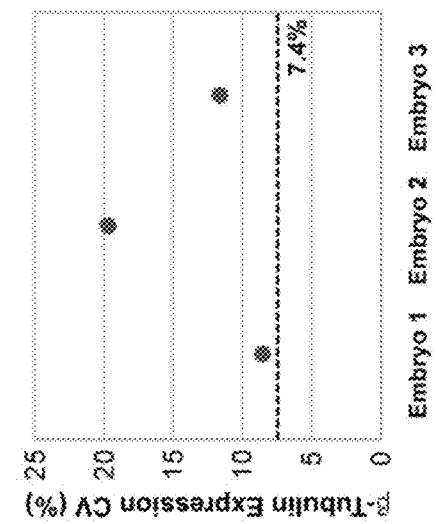
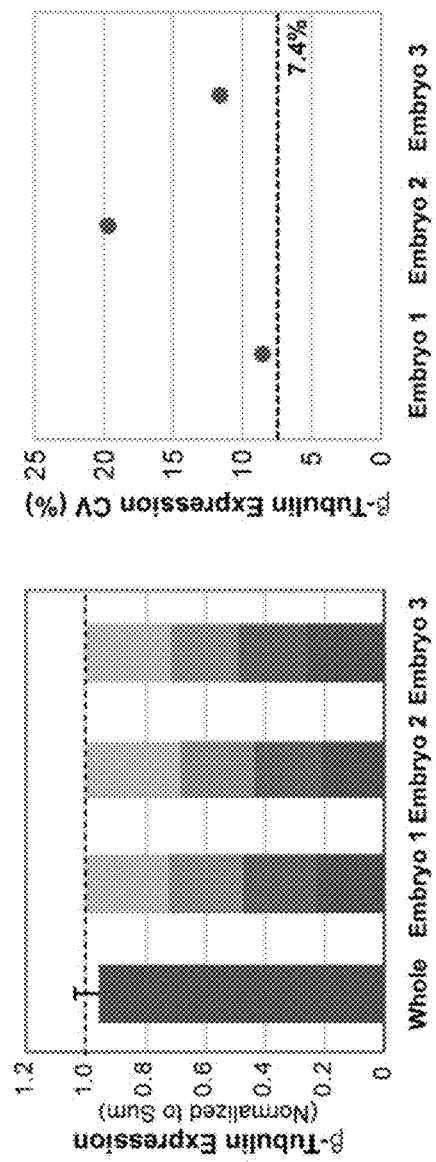
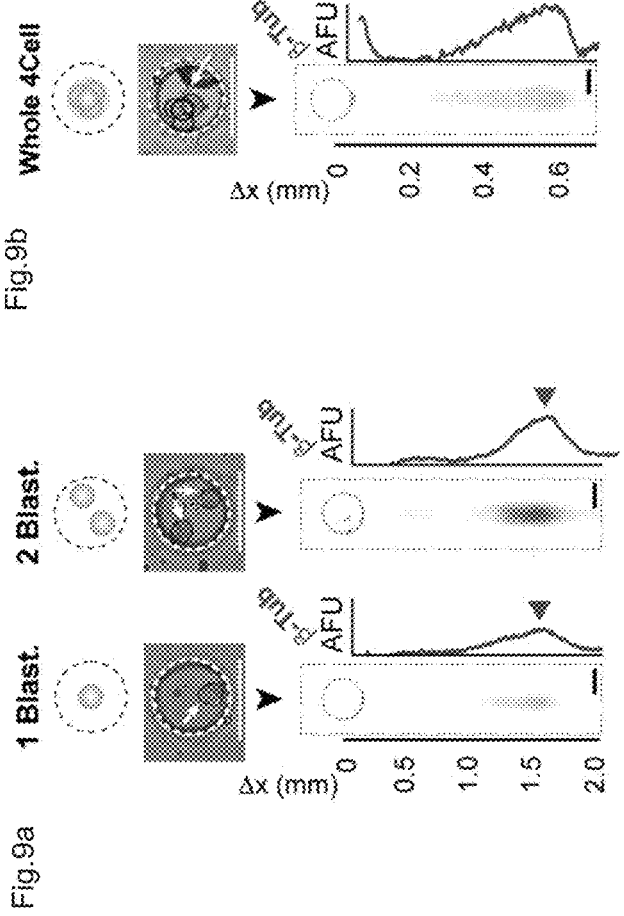
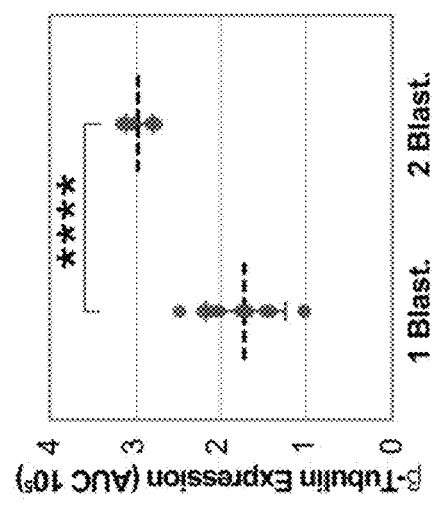
Fig.9b
Fig.9a

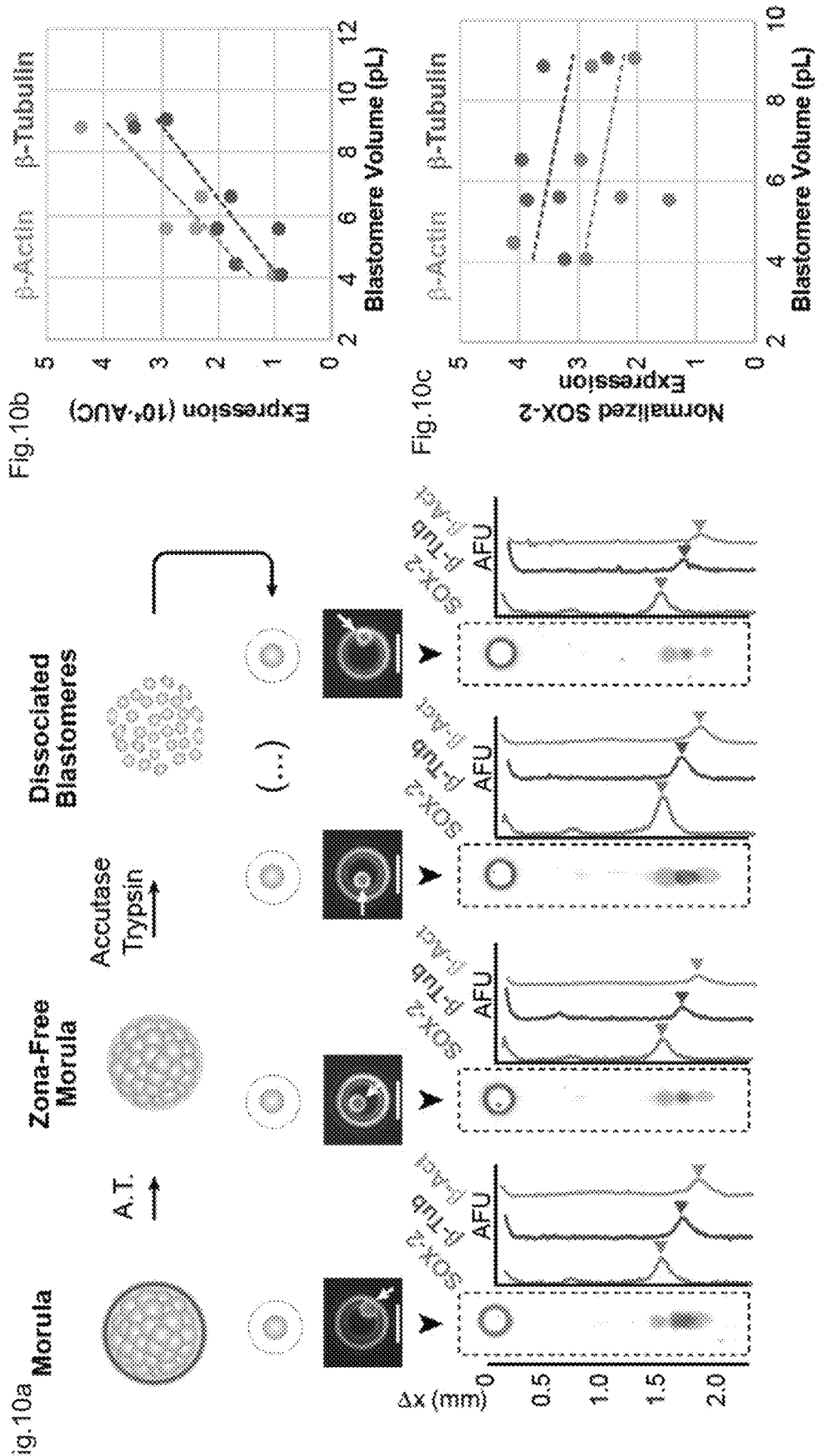

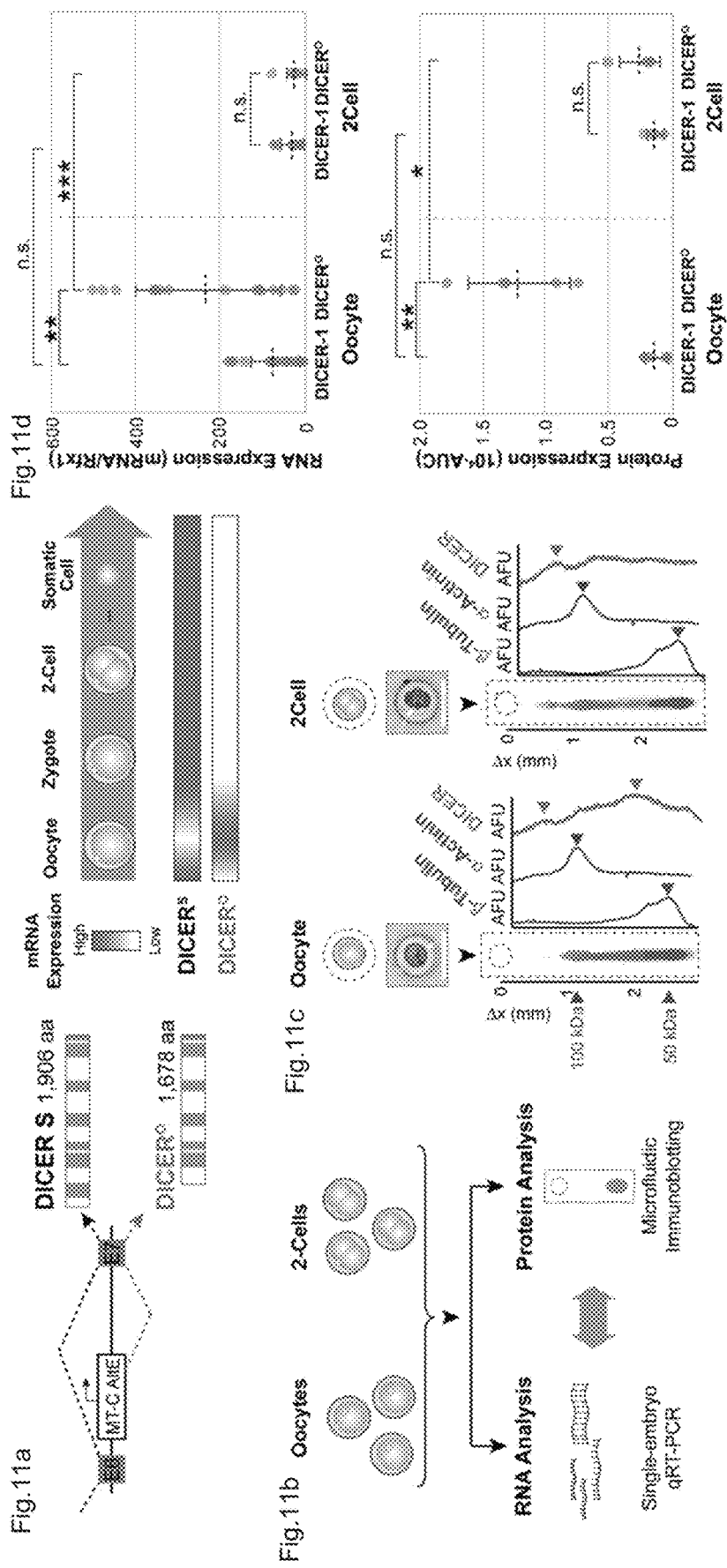

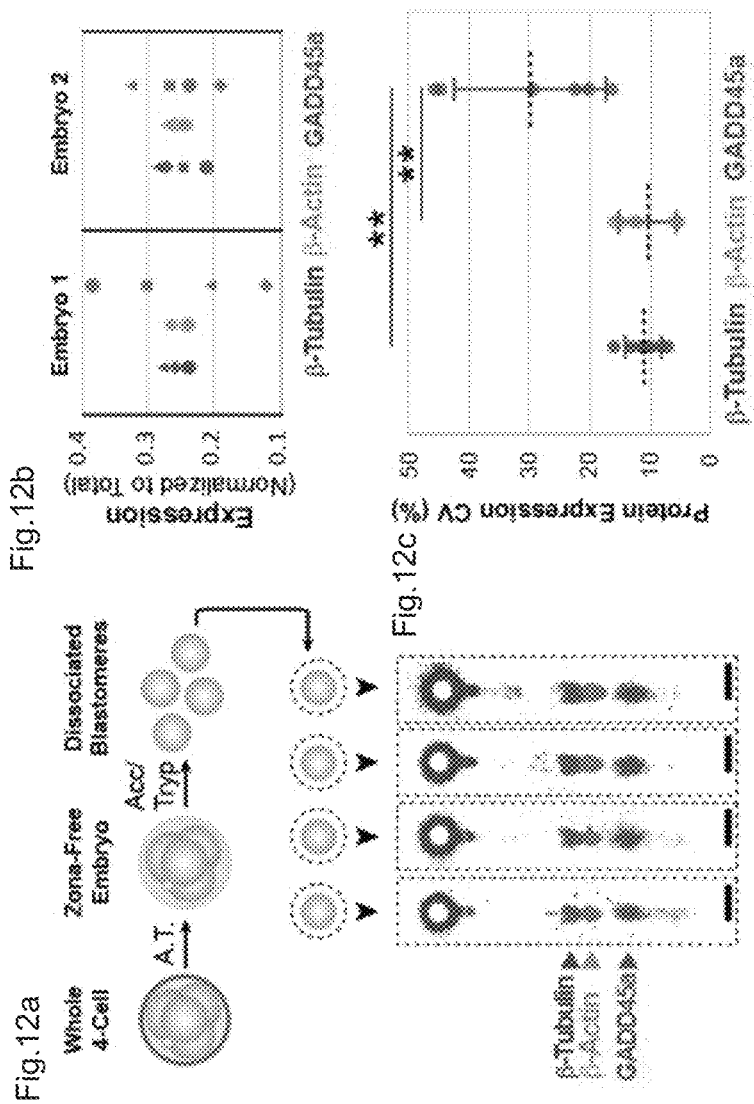

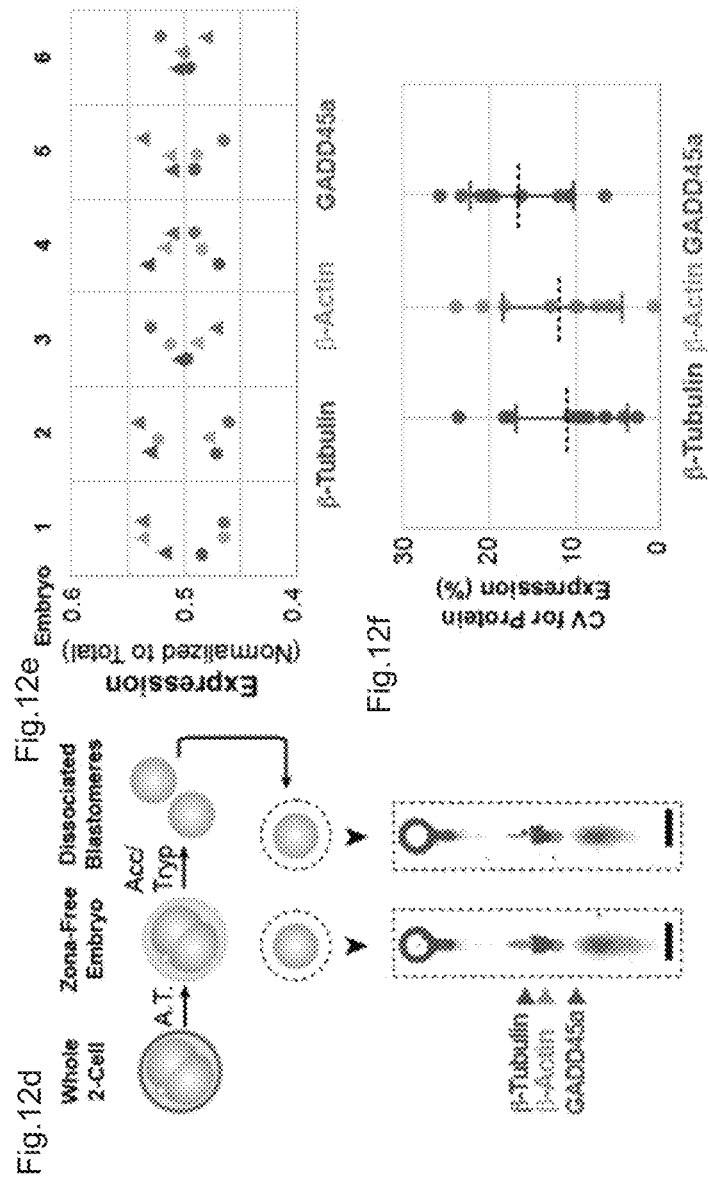

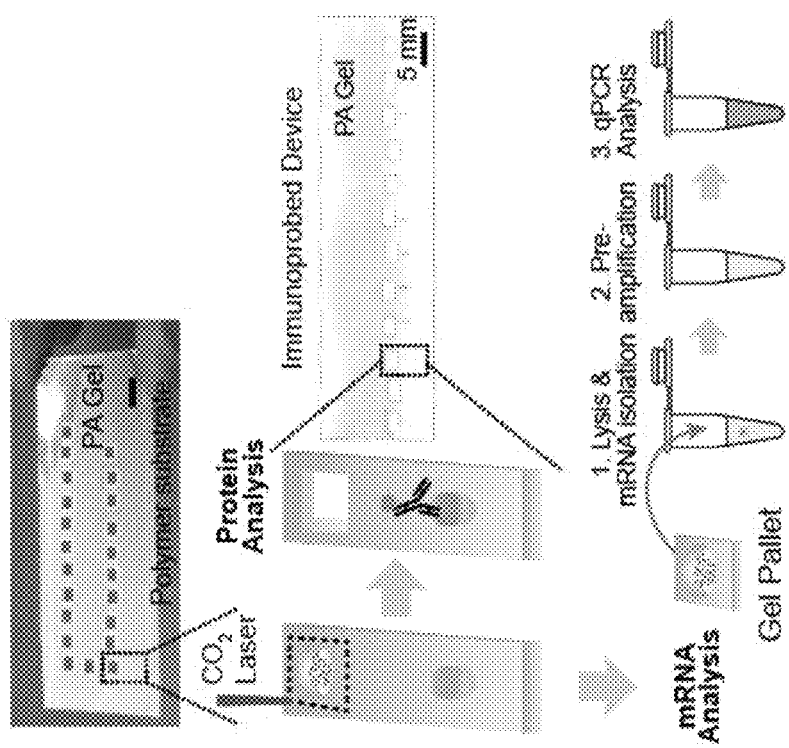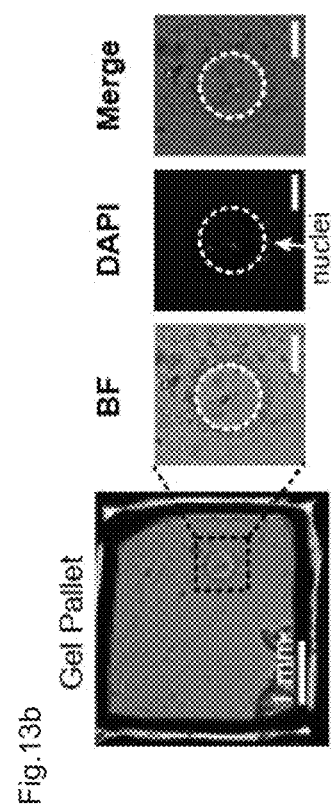
Fig. 13a
Fig. 13b

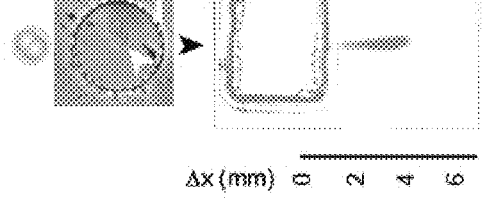
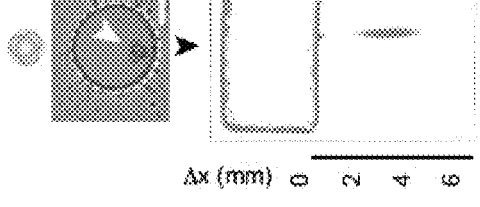
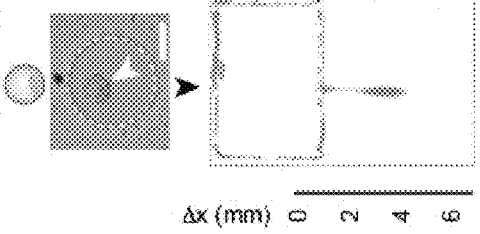
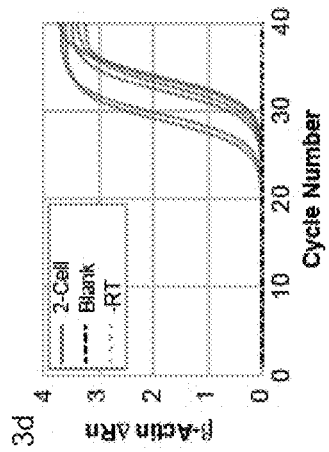
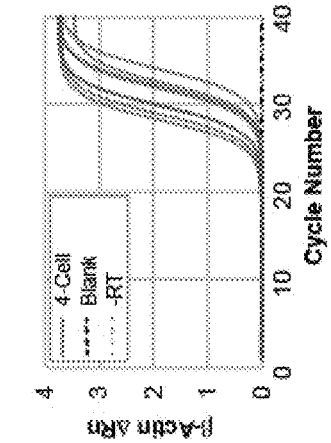
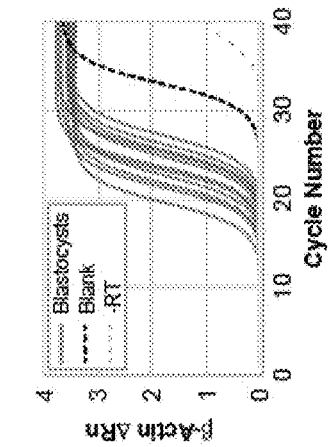
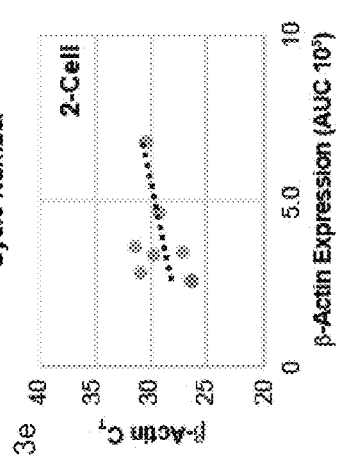
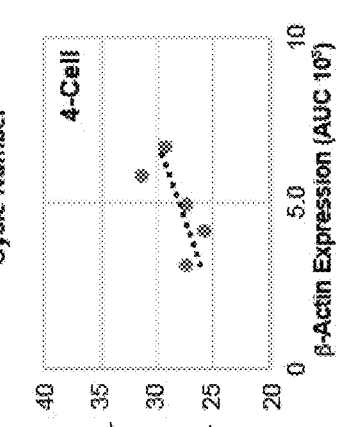
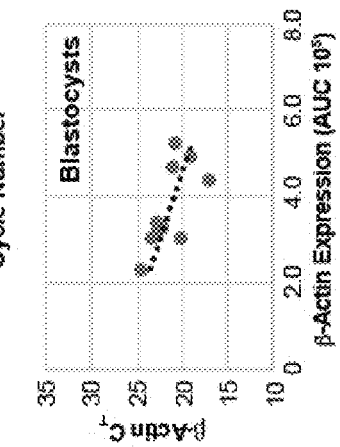
Fig.13c Fig.13d Fig.13e

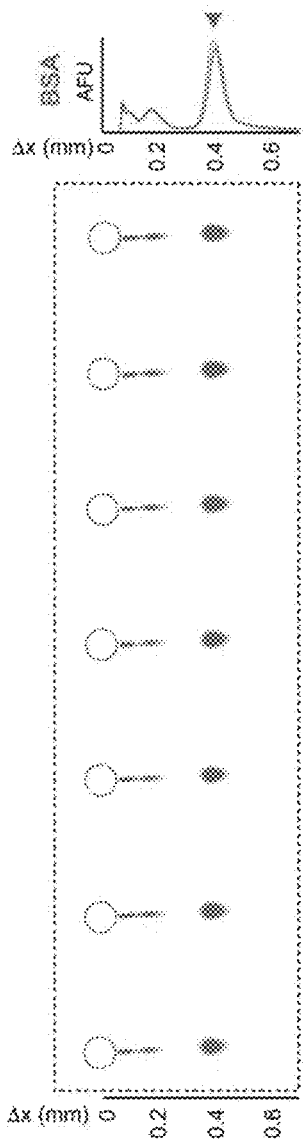
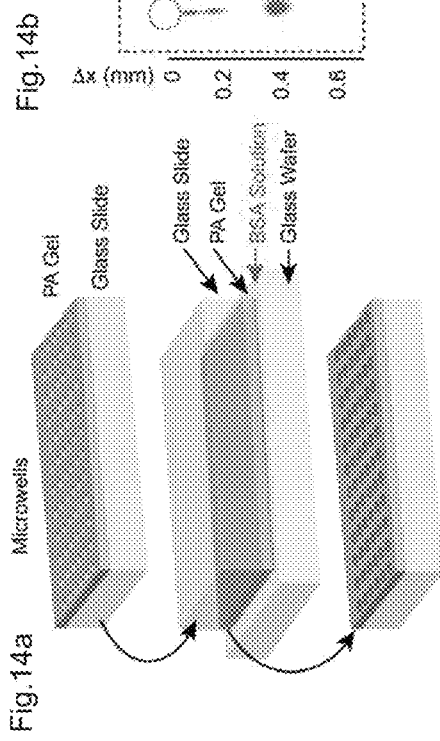
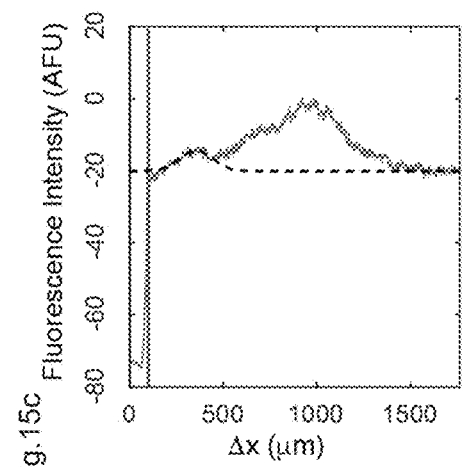
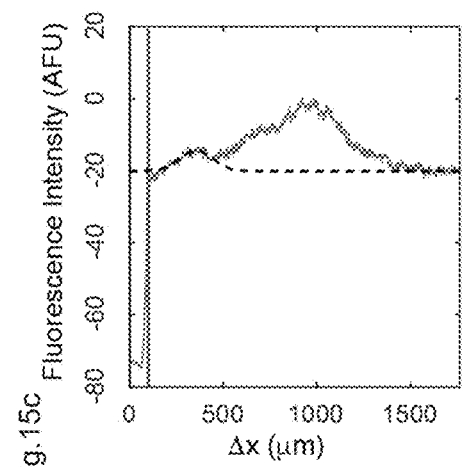
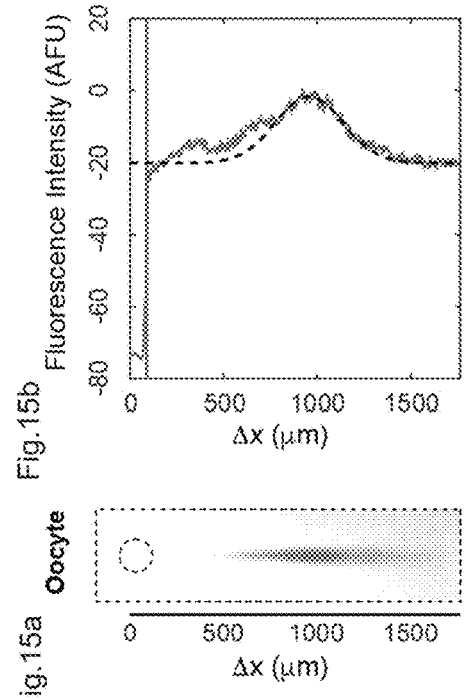

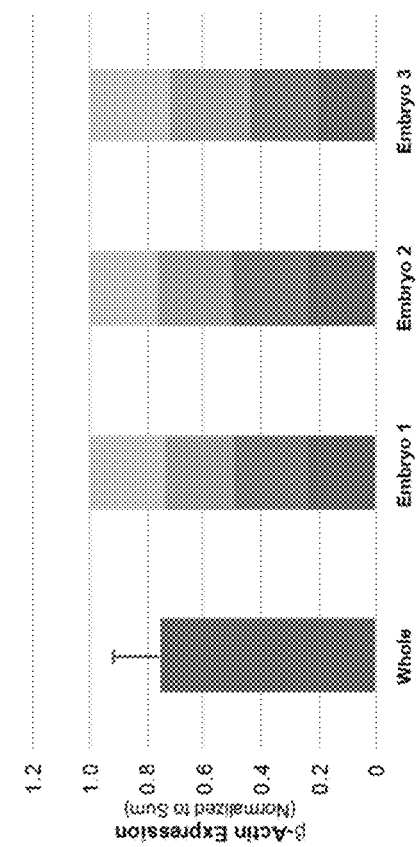
Fig. 18
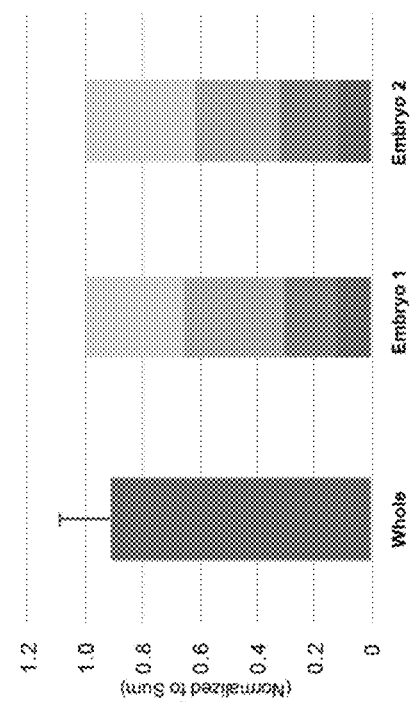
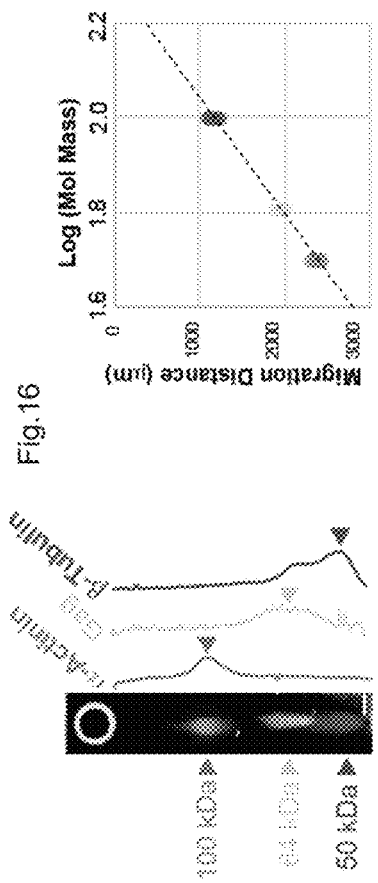
Fig. 16
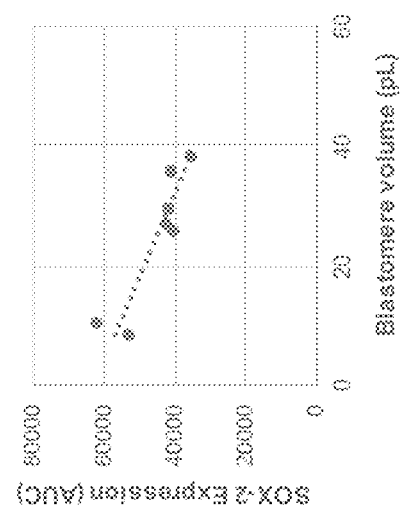
Fig. 17

SIMULTANEOUS DETECTION OF PROTEIN ISOFORMS AND NUCLEIC ACIDS FROM LOW STARTING CELL NUMBERS

This invention was made with government support under Grant Numbers CA139067, CA203018, GM114414, HD088885 awarded by the National Institutes of Health, and Grant Number 1056035 awarded by the National Science Foundation. The government has certain rights in the invention.

INTRODUCTION

Embryo-specific nucleic acid modifications, including retrotransposon activity-derived genomic modifications and alternative splicing of mRNA, are crucial for the development of mammalian embryos[1]. The importance of alternative splicing as a developmental regulatory mechanism, however, has been established by monitoring mRNA isoform levels and not protein levels. Resolving if all genomic modifications and mRNA isoforms translate to protein variations remains an intriguing question that requires simultaneously measuring (i) nucleic acids (DNA variations and mRNA isoforms) and (ii) protein isoforms in early-stage embryos.

Recently introduced technologies allow interrogation of the genome, epigenome, transcriptome, metabolome and protein at single-cell resolution[2-6]. Many tools now even measurement of proteins and DNA and/or RNA from single cells[2], allowing us to link genome, transcriptome and proteome. However, perform the protein measurements on different set of single cells than the nucleic acid measurements[2]. Furthermore, the specificity of the protein measurement of these methods relies on antibodies alone (which are subject to nonspecific cross-reactivity and cannot detect isoforms without isoform-specific antibodies), making it impossible to resolve protein isoforms when isoform-specific antibodies are not available. As a result, identifying different proteoforms arising from modifications to the DNA or mRNA therefore remains extremely challenging.

SUMMARY OF THE INVENTION

Here, we disclose a method for performing dual nucleic acid and protein isoform measurements on low starting cell numbers (1-100), a range that includes the cell numbers in the morula (16-30) and blastocyst (30-100) stages[7]. Our technique integrates fractionation polyacrylamide gel electrophoresis (fPAGE) with off-chip analysis of nucleic acids in the nuclei.

In an embodiment we designed polyacrylamide gel-based device, or GelBond™-PA gel device, comprising a 100-150 um polyacrylamide (PA) gel covalently grafted to a polyester film (GelBond™). After settling cells into microwells patterned on the PA gel, we perform fractionation single-cell polyacrylamide gel electrophoresis (fractionation PAGE). The plastic GelBond™ substrate allows us to then laser-excise areas of the gel, or gel rafts, containing the microwells with the fractionated nuclei. The nuclei-containing gel rafts are then collected to perform the genomic measurement, as well as transcriptomic measurements, given the conservation of general expression differences of genes between nuclei and whole cells[8,9]. In this way, we are able to measure expression of protein isoforms from the cytoplasmic fraction of 1-100 cells while achieving analysis of either DNA or mRNA retained in the nuclei.

In an aspect the invention provides a method for performing dual nucleic acid and protein isoform measurements on low starting cell numbers comprising: (a) performing fractionation polyacrylamide gel electrophoresis (fPAGE) of cells settled into microwells patterned on a 100-150 um polyacrylamide (PA) gel covalently grafted to a polyester film, wherein fractionated nuclei of the cells are retained in the microwells, and proteins of the cells are separated along a lane of the gel; (b) laser-excising areas of the gel, called gel rafts, containing the microwells with the retained, fractionated nuclei; (c) collecting and performing on the retained nuclei genomic and/or measurement, transcriptomic measurements; and (d) performing on the separated proteins one or more protein measurements.

In embodiments:
the method comprises measuring expression of protein isoforms from the cytoplasmic fraction of 1-100 cells and analyzing either DNA or mRNA retained in the nuclei;
the cells are blastomeres of a morula or blastocyst;
the method comprises diagnosis and/or prognosis for cancer, wherein the cells are obtained from biopsy or liquid biopsy, and/or any diseases where mutations to DNA or modifications to mRNA may be causing (i) differential expression of proteins, (i) expression of protein isoforms, or (iii) post-translational modifications in cells;
the method comprises gene editing, wherein the method provides validation of edited genes, and detection of on-target and off-target effects of gene editing; and/or
the method comprises simultaneous detection of nucleic acids and proteins in a single cell, single embryo, or single spheroid.

In an aspect the invention provides a polyacrylamide gel-based device, or GelBond™-PA gel device for performing dual nucleic acid and protein isoform measurements on cells, the device comprising a 100-150 um polyacrylamide (PA) gel covalently grafted to a polyester film, with microwells patterned on the PA gel, further comprising fractionated nuclei of the cells, retained in the microwells, and proteins of the cells, separated along a lane of the gel.

In embodiments:
the cells are blastomeres of a morula or blastocyst;
the device is configured for measuring expression of protein isoforms from the cytoplasmic fraction of 1-100 cells and analyzing either DNA or mRNA retained in the nuclei.
the device is configured for diagnosis and/or prognosis for cancer, wherein the cells are obtained from biopsy or liquid biopsy, and/or any diseases where mutations to DNA or modifications to mRNA may be causing (i) differential expression of proteins, (i) expression of protein isoforms, or (iii) post-translational modifications in cells;
the device is configured for gene editing, including validation of edited genes, and detection of on-target and off-target effects of gene editing; and/or
the device is configured for simultaneous detection of nucleic acids and proteins in a single cell, single embryo, or single spheroid.

The invention encompasses all combination of the particular embodiments recited herein, as if each combination had been laboriously recited.

BRIEF DESCRIPTION OF THE DRAWINGS

FIGS. 1a-1d: Fractionation PAGE is coupled with laser excision of microwells into gel rafts for off-chip analysis of nucleic acids. (a) The GelBond™-PA gel device is comprised of a thin polyacrylamide (PA) gel covalently grafted onto a GelBond™ polymer film substrate and stippled with microwells. 1-100 cells are settled into microwells of the GelBond™-PA device and lysed with fractionation buffer. An electric field is then applied to inject the solubilized cytoplasmic proteins into the PA gel and separate them by molecular mass, which are then immobilized to the gel by UV-light activation of benzophenone methacrylamide moieties in the PA matrix. A CO2 laser is then used to excise a region of the GelBond™-PA gel device that contains retained nuclei, creating a gel raft. The gel raft can then be analyzed off-chip for DNA or mRNA. The remaining GelBond™-PA gel device can be probed for proteins with fluorescently-labeled antibodies, yielding protein immunoblots from the original settled cells. (b) Fractionation PAGE retains nulcei in microwells. Top row displays bright field, DAPI and GFP micrographs of TurboGFP-U251 cells settled into a microwell of a GelBond™-PA gel device, prior to the cell lysis step. On bottom row, bright field, DAPI and GFP micrographs of microwell and PA gel abutting the microwell (separation lane) after fractionation PAGE, when cytoplasmic proteins have been electrophoresed into the PA gel while nuclei are retained in the microwell. (c) Excision of GelBond™-PA gel into gel rafts. Excision of microwells from GelBond™-PA gel creates gel rafts (left) that allow extraction of nuclei for off-chip analysis of nucleic acids. Bright field micrograph shows one gel raft. The retention of the nuclei can be verified by the fluorescence imaging of the Hoechst-stained nuclei, as displayed in the bright field, DAPI fluorescence and merged micrographs of a gel raft microwell. (d) Immunoblots of photocaptured and immunoprobed TurboGFP. On the left, false-colored micrograph of photocaptured TurboGFP protein after EP separation. Corresponding intensity profile is shown on adjacent to micrograph. On the right, false-colored micrograph of the immunoprobed TurboGFP immunblot, with corresponding intensity profile. Arrow heads mark the position of the protein peak.

FIGS. 3a-3d: Photocaptured and immunoblotted signal correlates with in-well fluorescence signal prior to lysis in turbo-GFP expressing cells. (a) Bright field and false-colored fluorescence micrographs of TurboGFP-expressing U251 cells settled into microwells, with corresponding false-colored fluorescence micrographs of TurboGFP immunoblots. Fluorescence intensity profiles are shown to the right of immunoblots, with black arrows marking the position of protein peaks. (b) Bivariate plot of whole-cell TurboGFP fluorescence prior to lysis (AFU) and photocaptured TurboGFP fluorescence (AUC) demonstrating a significant, positive linear correlation. (c) Bivariate plot of photocaptured and immunoprobed TurboGFP fluorescence (AUC) displaying a strong linear correlation. (d) Bivariate plot of whole-cell fluorescence prior to lysis (AFU) and immunoprobed TurboGFP fluorescence (AUC), also showing a positive linear correlation.

FIGS. 4a-4c: mRNA TurboGFP levels correlate with immunoprobed TurboGFP, but not whole-cell TurboGFP fluorescence and photocaptured TurboGFP. (a) Bivariate plot of whole-cell TurboGFP fluorescence prior to lysis (AFU) and TurboGFP mRNA normalized by GAPDH demonstrating a non-significant, positive linear correlation. (c) Bivariate plot of photocaptured and TurboGFP mRNA normalized by GAPDH demonstrating displaying a non-significant positive correlation. (d) Bivariate plot of immunoprobed TurboGFP fluorescence (AUC) and TurboGFP mRNA normalized by GAPDH demonstrating a significant positive linear correlation.

FIGS. 5a-5b: Set up for laser excision of PA gel device into gel rafts. (a) Schematic of PA gel device (left) and acrylic sheet onto which a 5 mm×5 mm grid has been engraved. PA gel device is placed with PA gel facing down onto the grid, so laser can cut through the GelBond™ film first, then the PA gel. (b) Top view of the PA gel and grid assembly. PA gel is aligned over the grid so that microwells are approximately 1 mm away from the top left edge of their corresponding grid square. Laser is aligned over the top left edge and programmed to cut a 3 mm×2 mm area, creating the gel raft.

FIGS. 6a-6c: Gel incubation set ups. (a) Schematic of the PA gel device structure. (b) Antibody solution incubation. PA gel device is placed facing down over a glass wafer. Antibody solution is pipetted between the PA gel and the glass wafer, allowing the solution to wick across the surface of the gel. (c) Schematic for hydrating gel in preparation for microarray scanner read-out.

FIGS. 7a-7d: Alternate protein detection immunoblotting and detection method. (a) Schematic of alternate GelBond™-PA-gel device, where the GelBond™ film forms a frame, or window, around the PA gel reinforced with Rhinohide® gel. (b) Schematic of protein separation, where proteins are separated in the x direction by application of an electric field. (c) Schematic of protein transfer from the GelBond™ gel film to a nitrocellulose or PVDF membrane in the z direction. (d) Proteins immobilized on the nitrocellulose or PVDF membrane are probed with fluorescently-labeled antibodies.

FIGS. 8a-8e Microfluidic immunoblotting of single embryos and single blastomeres measures protein and mRNA in murine preimplantation embryos. (a) The microfluidic immunoblotting workflow begins with sampling a single embryo or single blastomere into a microwell patterned on a polyacrylamide (PA) gel. Samples are lysed and electrophoresed into the PA, achieving separation of proteins by molecular mass. Proteins are photo-blotted, or immobilized to the gel matrix by UV-activated benzophenone chemistry, and probed with fluorophore-conjugated antibodies. (b) Loading control β-tubulin was measured from single oocytes down to single blastocyst blastomeres. Brightfield micrographs of a settled oocyte and blastomere are shown above false-colored micrographs of resulting β-tubulin immunoblots and corresponding fluorescence intensity profiles. Arrows mark position of protein bands and scale bars are 100 μm, unless specified. (c) Single morula assayed for multiple targets that differ by 1-2 kDa (GAPDH, CDX-2 and SOX-2) show a strong log-linear relationship between migration distance and molecular mass ($R^2$=0.9842). (d) The same-embryo mRNA and protein analysis device consists of a PA gel grafted to a polymer film. The cytoplasmic fraction of embryos sampled into wells is first lysed and electrophoresed across the PA layer. Separated proteins are photoblotted to the matrix and probed with antibodies as in panel (a). A $CO_2$ laser cutter is used to extract sections of the PA-polymer film device, termed gel pallets, that contain nuclei retained in the microwells. mRNA is then isolated from gel pallets and analyzed for targets by RT-qPCR. Negative controls include blanks (gel pallets that did not contain nuclei), -RT and NTC. (e) Bar graph of β-actin CT results after performing RT-qPCR on gel pallets containing single blastocyst nuclei and blanks.

FIGS. 9a-9b Microfluidic immunoblotting detects intra-embryonic biological variation in β-tubulin expression. (a) β-tubulin titration experiment. One or two blastomeres of dissociated four-cell embryos are sampled into microwells and assayed for β-tubulin. Brightfield images show blastomeres settled into microwells prior to lysis. Under these, false-color fluorescence micrographs and corresponding β-tubulin intensity profiles of resulting immunoblots. Arrows mark the position of protein bands. Dot plot of β-tubulin signal for immunoblots of one and two blastomeres demonstrate an increase in detection of β-tubulin for two blastomeres over one blastomere. (b) Reconstruction of whole embryo from disaggregated blastomeres. Bright field micrographs of whole and disaggregated four-cell embryos settled into microwells (top), with corresponding false-color fluorescence micrographs of β-tubulin immunoblots. Intensity profiles are shown to the right of immunoblots, with blue arrow marking the position of the protein bands. Stacked bar graphs show individual blastomere contributions to total β-tubulin expression of four-cell embryos. Whole embryos assayed alongside dissociated blastomeres show similar levels of total β-tubulin expression, indicating sum of individually assayed blastomeres is equivalent to a whole embryo. Dot plot of B-tubulin expression coefficient of variation (CV %) for blastomeres of three disaggregated four-cell embryos. All CV values are above the technical $CV_{threshold}$ of 7.4% (FIG. 14).

FIGS. 10a-10c Single-blastomere immunoblotting identifies correlations between cell volume and marker expression in dissociated morula blastomeres. (a) Immunoblotting dissociated morula blastomeres for β-tubulin, β-actin and SOX-2. Schematic (top) for dissociation of whole morula into individual blastomeres, which are seated into microwells of an immunoblotting device as shown in bright field images. False-colored fluorescence micrographs show tubulin, actin and SOX-2 protein bands, with intensity profiles adjacent to micrographs. Arrows mark the position of protein bands. Scale bars are 100 µm. (b) Bivariate plot of blastomere cell volume and loading control expression (β-tubulin and β-actin) shows significant positive linear correlation. (c) Bivariate plot of cell volume vs. SOX-2 expression normalized by β-tubulin and β-actin expression show a negative, but non-significant, association.

FIGS. 11a-11d Higher DICER-1 isoform expression in oocytes than in two-cell embryos correlates with mRNA levels. (a) $DICER^O$, a truncated isoform of DICER-1, appears only at the oocyte stage and is a product of alternative promoter usage. (b) Schematic of oocytes and two-cell embryos analyzed either by microfluidic immunoblotting or by companion qRT-PCR analysis. (c) Bright field micrographs of a settled oocyte and two-cell embryo. Under these, corresponding overlaid false-color fluorescence micrographs and intensity profiles show protein bands for loading controls (α-actinin and β-tubulin) and DICER-1, where oocyte immunoblot demonstrates presence of a full-length DICER-1 (top arrow) and a lower molecular mass isoform (bottom arrow). Scale bars are 100 µm. (d) Dot plots of DICER isoform mRNA levels normalized by endogenous control Rfx1 (top) and protein expression (AUC, bottom) for single oocytes and single two-cell embryos. Expression of the truncated isoform is higher than the full-length DICER-1 for both mRNA and protein in oocytes, but not in two-cell embryos. Oocytes show higher mRNA and protein expression than two-cells for the truncated isoform, but not the full-length DICER-1.

FIGS. 12a-12f. Microfluidic immunoblotting measures intra-embryonic heterogeneity in GADD45a expression in four-cell and two-cell embryos. (a) Design for testing GADD45a heterogeneity in four-cell embryos. Zona pellucida is removed and four-cell embryos are dissociated into individual blastomeres for subsequent immunoblotting for GADD45a and loading controls β-tubulin and β-actin. False-color fluorescence micrographs for one dissociated four-cell embryo assayed for protein targets, with intensity profiles shown to the right. (b) Dot plot of expression of β-tubulin (blue), β-actin (cyan) and GADD45a (red) normalized to total expression, by individual blastomeres from two representative four-cell embryos. (c) Dot plot of inter-embryonic coefficient of variation (CV) in protein expression for β-tubulin, β-actin and GADD45a. (d) Schematic of two-cell embryo sample preparation by removal of zona pellucida and dissociation into individual blastomeres. False-color fluorescence micrographs show ß-tubulin, β-actin and GADD45a immunoblots for two-cell sister blastomeres. (e) Dot plots of ß-tubulin and GADD45a expression by sister blastomeres, normalized to sum of expression of sister blastomeres, for six representative two-cell embryos. (f) Dot plot of inter-blastomeric CV % in expression of β-tubulin, β-actin and GADD45a. Same marker for a given embryo in (b) and (d) indicate same blastomere. Horizontal bars in (c) and (f) indicate mean+S.D. Scale bars are 100 µm.

FIGS. 13a-13e Same-embryo mRNA and protein expression analyses show positive correlation for late-stage pre-implantation embryos, but not two-cell and four-cell embryos. (a) Device image and workflow for same-cell mRNA and immunoblotting analysis. After single-embryo PAGE and photo-blotting (protein immobilization), microwell-isolated nuclei are collected for off-chip mRNA analysis: 1. Lysis & mRNA isolation, 2. Pre-amplification, 3. qPCR Analysis. To collect each nucleus, a gel pallet housing the nucleus-laden microwell is excised (by $CO_2$ laser) and suspended in fluid. Immunoprobing is performed on protein targets blotted to the gel remaining on the microfluidic device. (b) Micrographs of a gel pallet housing Hoechst-stained nuclei. Scale bars are 50 µm unless specified. (c) Brightfield micrographs show intact two-cell, four-cell, and blastocyst-laden microwells. False-color fluorescence micrographs show resulting β-actin immunoblots, with rectangular perimeter of excised gel pallets visible in micrographs and corresponding intensity profiles shown to the right. (d) RT-qPCR β-actin amplification curves for two-cell, four-cell, and blastocyst-stage embryos and corresponding negative controls (-RT and blank controls consisting of empty gel pallets). (e) β-actin mRNA CT values and protein expression levels (AUC) for two-cell, four-cell, and blastocyst-stage embryos. Dashed lines show best linear fits.

FIGS. 14a-14b Determination of the technical variation threshold of the microfluidic immunoblot. (a) Schematic of purified protein immunoblotting assay. The polyacrylamide (PA) gel of the microfluidic immunoblotting device is incubated with a solution of fluorescently-labeled bovine serum albumin (BSA) for 30 min for BSA to partition into microwells. Assay is then run as described in main text. (b) False-color fluorescence micrograph of resulting BSA immunoblots (left) and corresponding fluorescence intensity profiles used to perform area-under-the-curve (AUC) quantification (right). The coefficient of variation (CV %) was calculated as S.D./mean×100 for N=9 replicates. The technical variation threshold was computed as the mean CV (4.7%) plus three standard deviations for a 99% confidence interval (S.D.=0.9%) yielding a CV threshold of 7.4%.

FIGS. 15a-15c Intensity profiles and Gaussian fits for DICER-1 isoforms. (a) Fluorescence micrograph of a single oocyte immunoblotted for DICER-1. (b) Fluorescence intensity profile corresponding to the micrograph in (a) with Gaussian curve fit to the DICER$^o$ isoform (low molecular mass, $R^2$=0.83). (c) Fluorescence intensity profile for DICER-1 with Gaussian curve fit to the DICER-1 full-length isoform ($R^2$=0.89). Gray solid lines mark the position of the microwell wall.

FIG. 16 Validation of electromigration behavior for a wide 50 to 100 kDa protein mass range. On the left, false-color fluorescence micrograph of a two-cell embryo immunoblotted for α-actinin (green), Gag (yellow) and β-tubulin (blue). Corresponding intensity profiles are shown to the right, with arrows marking position of protein peaks. On the right, bivariate plot of migration distance and log of molecular mass, showing a linear correlation with $R^2$ of 0.904 for N=16.

FIG. 17 SOX-2 expression in single blastomeres disaggregated from blastocysts. Bivariate plot of SOX-2 expression and blastomere volume computed from bright field images of settled blastomeres, where SOX-2 expression shows a significant negative correlation with blastomere volume.

FIG. 18 β-actin and GADD45a expression from disaggregated and whole four-cell embryos. Stacked bar graphs show individual blastomere contributions to total β-actin or GADD45a expression of four-cell embryos. Whole and disaggregated embryos show similar levels of total expression.

DESCRIPTION OF PARTICULAR EMBODIMENTS OF THE INVENTION

Design of assay for measuring protein and nucleic acids from the same 1-100 mammalian cells. In order to perform dual protein-nucleic acid measurements on the same 1-100 mammalian cells, we designed an assay that integrates (i) electrophoretic separation of cytoplasmic proteins and (ii) extraction of nucleic acids from the nuclei.

Our assay begins with settling cells into the microwells patterned onto the GelBond™-PA gel device, a 200 um-thick polyacrylamide (PA) gel covalently bound to the treated surface of a flexible polyester film (Gelbond™ PAG Film) (FIG. 1a, left image). After cells are settled into microwells by gravity, a buffer exchange step from PBS to a fractionation lysis buffer[9] achieves in situ lysis of the cytoplasmic fraction of cells (FIG. 1a). An electric field is then applied to (i) inject solubilized proteins through the microwell wall and into the PA gel layer and (ii) achieve polyacrylamide gel electrophoresis (PAGE), which separates proteins by molecular mass along the separation lane, or region abutting the microwell. Proteins are then photocaptured by UV-light activation of benzophenone moieties incorporated in the PA gel matrix. After cytoplasmic protein PAGE, the nuclei remain intact in the microwells. Nuclei are extracted from the device by $CO_2$ laser-excision of a 2 mm×3 mm area of the GelBond™-PA device into gel rafts containing the intact nuclei. These gel rafts are then placed into reaction vessels in order to perform extraction and off-chip analysis of either DNA or mRNA. The remaining GelBond™-PA gel device is then probed for proteins with fluorescently-labeled antibodies, yielding protein immunoblots from the original settled cells.

Figures 2A, 2B:
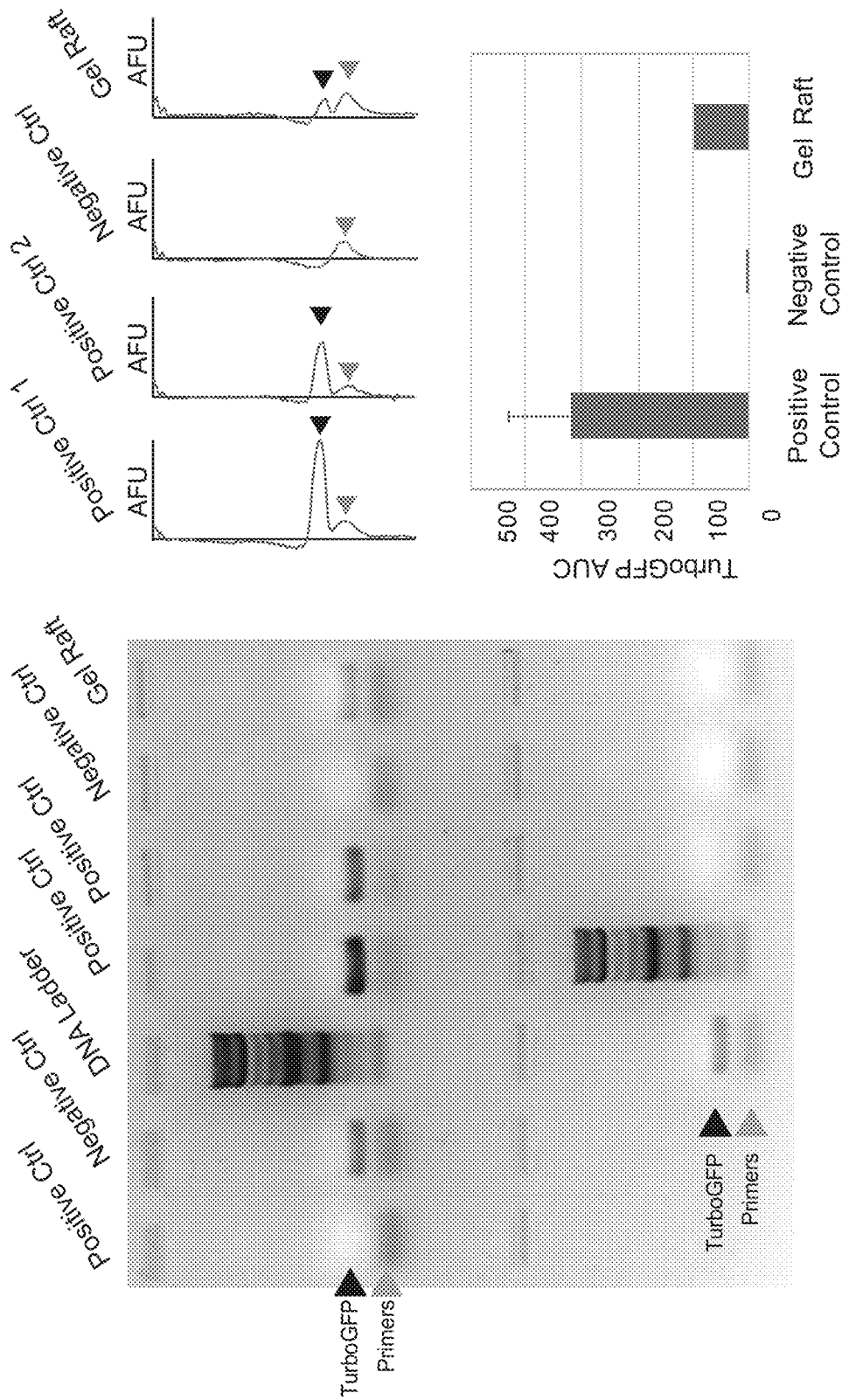
FIG. 2a-2b: PCR amplification of DNA from a gel raft containing a single nucleus. (a) Agarose gel electrophoresis of DNA amplified for the TurboGFP gene by PCR from samples including positive controls (10 ug DNA extracted from TurboGFP-U251 lysate), negative controls (no DNA) and gel raft containing one TurboGFP-U251 nucleus. (b) Intensity profiles for agarose gel lanes corresponding to positive controls, negative control and the gel raft that contained a single TurboGFP-U251 nucleus. The gel raft band shows a 78-fold increase with regards to the negative control and 33-fold decrease with respect to the positive control.

In order to optimize our workflow, we utilized TurboGFP-transduced U251 human glioblastoma cells, where the expression of fluorescent TurboGFP was a useful protein model for visualizing protein lysis, injection, PAGE and photocapture. We first settled TurboGFP-U251 cells stained with nuclear Hoechst dye settled into a microwell of a GelBond™-PA gel device (FIG. 2b, top). After fractionation lysis, PAGE and photocapture, we observed a TurboGFP band in the separation lane along with absence of TurboGFP fluorescence in the microwell, suggesting complete lysis and injection of the cytoplasmic proteins into the PA gel has been achieved (FIG. 2b, bottom).

Next, after placing the GelBond™-PA gel device in nuclei wash buffer in order to maintain the integrity of the nuclei, we excised gel rafts containing the microwells (FIG. 2c, left). Fluorescence imaging of the Hoechst-stained nuclei confirmed the presence of the nuclei in the microwells (FIG. 2c, right). The remaining GelBond™-PA gel device was imaged for native TurboGFP signal and then incubated with primary antibodies against TurboGFP followed by AlexaFluor555-conjugated secondary antibodies and imaged for resulting TurboGFP immunoblots (FIG. 2d).

Laser excision into gel rafts does not compromise integrity of nuclei.

To validate the integrity of nuclei and viability of nucleic acid analysis after retrieval, we aimed to perform amplification of the TurboGFP gene by polymerase chain reaction (PCR) from gel rafts containing a single nucleus. We designed microwells to isolate single TurboGFP-expressing U251 cells (32 um in diameter, 40 um in height). After fractionation and PAGE of the cytoplasmic fraction, single nuclei retained in the microwells were excised into gel rafts. We inspected gel rafts under an epifluorescence microscope for the Hoechst-stained nuclei to verify retention of the nucleus. Gel rafts were then placed into separate reaction vessels (centrifuge tubes) for PCR amplification of the TurboGFP gene. PCR products were analysed on an agarose gel, revealing successful amplification of the TurboGFP from the gel raft (FIG. 2b, 2c). A 78-fold increase with regards to the negative control of the gel raft band, and 33-fold decrease with respect to the positive control indicates amplification of TurboGFP gene from the gel raft sample, validating viability of DNA extraction from nuclei in gel rafts.

Photocaptured and immunoblotted protein fluorescence signal correlates with protein expression prior to lysis We next evaluated whether protein measured after lysis, EP separation and immunoblotting accurately measures protein abundance prior to lysis. We used the TurboGFP protein in TurboGFP-expressing U251 cells as our protein target in order to use fluorescence as a convenient measure of protein abundance. We first imaged TurboGFP-U251 cells settled into microwells prior to lysis and computed fluorescence intensity (AFU). We then ran fractionation PAGE and scanned the PA gel device for photocaptured, native TurboGFP fluorescence. We calculated total fluorescence by performing area-under-the-curve (AUC) analysis. Finally, we immunoprobed the PA gel devices with primary antibodies against TurboGFP (rabbit-anti-TurboGFP), followed by fluorophore-conjugated secondary antibodies (AlexaFluor555 donkey-anti-rabbit), and computed total immunoprobed signal (AUC).

When comparing (i) whole-cell TurboGFP prior to lysis, (ii) native signal from the photocaptured TurboGFP and (iii) immunoprobed signal from fluorophore-conjugated antibodies against TurboGFP (FIG. 2a), we found that whole-cell TurboGFP fluorescence demonstrated a significant positive, linear correlation with signal from both photocaptured TurboGFP and immunoblotted fluorescence signal (FIG. 2b, 2c). Likewise, photocaptured and immunoblotted signal showed a significant positive, linear correlation (FIG. 2d). These results indicate that measuring signal from resulting immunoblots accurately estimates protein abundance in cells prior to lysis, EP and photocapture.

TurboGFP mRNA levels show higher correlation with TurboGFP immunoprobed signal than signal from whole-cell fluorescence and photocaptured TurboGFP We finally examined whether we could recover and measure mRNA from excised microwells. After fractionation PAGE and excision of Gelbond™-PA gel into gel rafts, gel rafts were placed into separate reaction vessels containing TRIzol in order to extract mRNA from the intact nuclei in gel rafts.

Isolated RNA was analyzed for TurboGFP and reference gene GAPDH using quantitative real-time PCR analysis (qRT-PCR). Results show that whole-cell fluorescence and photocaptured protein signal do not show a significant correlation with mRNA levels (FIG. 4a-b). On the other hand, TurboGFP mRNA levels interestingly show a significant positive association with immunoprobed TurboGFP signal (FIG. 4c).

Interestingly, immunoprobed TurboGFP is the only protein signal significantly correlated with TurboGFP mRNA. These results suggest that native TurboGFP fluorescence may not be an accurate proxy for protein abundance because it requires correct folding of the TurboGFP protein. Immunoprobing, on the other hand, is performed in denaturing conditions in order to ensure epitopes of all proteins are available to antibodies. These results indicate the ability to measure unlabeled endogenous proteins, where the starting concentration prior to lysis cannot be determined through fluorescence.

Conclusion. Assessing whether specific modifications in genomic DNA and frequent alternative splicing drive important mechanisms in preimplantation development requires measuring both nucleic acids and protein isoforms. Here we designed an assay for simultaneous measurement of protein isoforms and nucleic acids from low starting numbers of mammalian cells. We demonstrated that signal from immunoprobed protein correlates strongly with protein expression prior to lysis in TurboGFP-expressing cells. We also measured both mRNA and DNA from retrieved nuclei, with positive amplification of TurboGFP gene and mRNA, demonstrating our ability to recover, isolate and amplify nucleic acids from gel rafts. The cell number range over which we performed these measurements (from 1 to approximately 100 cells) includes the cell numbers in the latest stages of the preimplantation embryo, the morula (16-30) and blastocyst (30-100). The application of this tool to morula and blastocysts further demonstrates the mechanisms by which embryo-specific nucleic acid modifications to both genomic DNA and mRNA orchestrate the growth and development of mammalian embryos. More broadly, the ability to extract the nuclei for off-chip analysis enables any nucleic acid measurement, including RNA-Seq, to be performed along with the simultaneous protein measurement.

Device Fabrication. SU-8 wafers, fabricated by photolithography as previously reported[10], were used as molds to cast PA gel devices. SU-8 posts on wafers, which later translate into microwells in the PA gel, were 200 um in diameter and 200 um in height. Briefly, PA precursor solution including acrylamide/bis-acrylamide (10% T) and 3 mM BPMAC was degassed with sonication for 9 min. 0.08% APS and 0.08% TEMED were added to precursor solution and solution was pipetted between the SU-8 wafer (rendered hydrophobic with Gel Slick™ solution) and a GelBond™ Film cut to the size of a standard glass microscope slide (25 mm×75 mm). After chemical polymerization (20 min) the GelBond™-PA gel devices (thin PA gel layer covalently grafted onto the GelBond™ surface) were lifted from wafer, rinsed with deionized water and stored in hydrated (DI water) at 4° C. until use.

Example: Combined mRNA Analysis and Immunoblotting Using Single Embryos and Single Blastomeres In this example we describe a high-specificity microfluidic immunoblot optimized to quantify protein expression from all stages of mouse preimplantation development and introduce a novel tool that allows for mRNA and protein measurements on the same single embryo. At the morula stage, we assayed both whole and disaggregated embryos for loading controls (β-tubulin, GAPDH and β-actin) and markers that regulate cell fate decisions (CDX-2, SOX-2), showing in disaggregated morula that cell volume correlates with expression of loading controls β-tubulin and β-actin. In dissociated four-cell blastomeres, we detect significant inter-blastomeric variation in GADD45a expression, corroborating suspected cellular heterogeneity in early multicellular stages of preimplantation embryos. Despite limited availability of isoform-specific immunoreagents, the immunoblot resolves inter-embryonic heterogeneity of embryo-specific isoforms (i.e., DICER-1). We observed significantly higher DICER-1 isoform expression in oocytes when compared to two-cell embryos, and further find that protein expression levels follow the same trend as mRNA for both the full-length and truncated DICER-1 isoforms. Due to maternal inheritance and zygotic genome activation, the correlation between mRNA and protein has been historically difficult to study in the preimplantation embryo. When performing same-embryo protein and mRNA analysis, we find an initial poor correlation between β-actin protein and mRNA expression at the two-cell and four-cell stage, that becomes significant at the blastocyst stage. The strategy demonstrated here provides a means to resolve transcriptional and translation questions revolving around zygotic genome activation. As RNA-Seq and other transcript-centric advancements continue to probe preimplantation development, the demand for companion protein-based techniques is steadily rising. The microfluidic immunoblot reported here provides high-specificity and direct measurements of protein targets at single-embryo and single-blastomere resolution. Further, the integration of a nucleic acid measurement enables simultaneous protein and mRNA measurements on the same single embryos, providing an essential tool for determining how the interplay between mRNA and protein expression orchestrates preimplantation development.

Introduction. The initiating events and proteins involved in the first cell fate commitment within pre-implantation blastomeres still constitute important open questions in developmental biology. While functional studies and embryonic plasticity suggest that blastomeres remain equivalent until the compacted morula[1-3], growing evidence of inter-blastomeric differences in early-stage embryos point to heterogeneous configurations at even the earliest multicellular stages[4,5,14,6-13]. Although transcriptional measurement tools with single-embryo and single-blastomere resolution have greatly advanced our knowledge, companion protein expression and state measurements within single embryos are required to test and unequivocally validate these transcript-based predictions. The need for direct assessment of protein expression in single cell studies is steadily rising.

While immunofluorescence (IF) can report protein abundance and localization in embryos, IF is stymied by: (i) ubiquitous immunoreagent cross-reactivity that renders IF unsuitable for detection of small protein variations or multiplexing beyond ~5 targets[15], (ii) proteoform 'blind spots' arising from limited isoform-specific immunoreagents that reduce the detectable repertoire of targets[16], and (iii) confounding but necessary chemical fixation prior to IF measurements of endogenous intracellular proteins (i.e., epitope masking, cell morphology modifications, and perturbation of protein localization by diffusional gradients formed as fixation occurs)[17,18]. Flow cytometry and mass cytometry suffer from similar specificity and fixation concerns as IF[19]. Recent advances in bottom-up mass spectrometry afford single-cell sensitivity$_{20,21}$. To measure proteoform stoichiometry, however, mass spectrometry of intact proteins (i.e., top-down) is needed to grant insight not obtainable from digested samples used in bottom-up approaches. Mass spectrometry of intact proteins remains challenged by sensitivity, multiplexing and protein identification limits[22]. Further, benchtop approaches that complement wide-coverage discovery tools are lacking[20,21]. Although high specificity, electrophoresis-based protein analysis tools have recently been introduced for analysis of un-fixed single cells and sub-cellular protein localization[23-28], fundamental inconsistencies between cultured cell lines and mammalian embryos have prevented the technical transition to the study of early mammalian development. Critical differences that need to be overcome include cell size and composition, membrane structure, embryo handling, and low sample availability (~10-20 embryos per mouse, depending on strain)[29-32]. To complement the repertoire of existing measurements, precision protein tools with higher selectivity are needed.

Resolving the intriguing questions surrounding mammalian development, such as when and how the first cell fate decisions are made, is further hindered by challenges with measuring mRNA and protein expression simultaneously. While single-cell mRNA analysis techniques, such as RNA-seq, have greatly advanced our understanding of the transcriptional landscape of the preimplantation embryo$_{4,10,33}$, these measurements very often do not necessarily correlate with protein[34]. Current techniques for measuring mRNA and protein from the same single cells use either fluorescence in situ hybridization (FISH)[35,36], proximity ligation[37], or standard single-cell mRNA sequencing approaches[38] to quantify mRNA, in combination with immunofluorescence[36], flow or mass cytometry[35], or proximity ligation[34] to detect proteins. Additionally, oligo-labeled antibodies enable protein probes to be mapped to nucleic acids, allowing probes for both mRNA and protein to be amplified and measured using either qPCR or single-cell RNA sequencing workflows[38]. However, existing methods do not resolve isoforms using size, charge, or other physicochemical properties useful in overcoming the limited specificity of immunoprobes. While capillary electrophoresis to separate and detect both mRNA and protein from cell lysates has been reported[39], this approach does not provide single-cell resolution and does not have the specificity to distinguish specific mRNA sequences or specific protein molecules.

Here we report microfluidic immunoblotting for direct analysis of proteoforms across all stages of mouse preimplantation, from whole embryos to single blastomeres and introduce the novel capability of performing both immunoblotting and mRNA analysis on the same sample. Microfluidic immunoblotting, alone or in combination with mRNA analysis, provides the resolution necessary to quantifiably investigate both inter- and intra-embryonic heterogeneity.

Microfluidic Immunoblotting of Single Embryos and Single Blastomeres

Figure 8A:
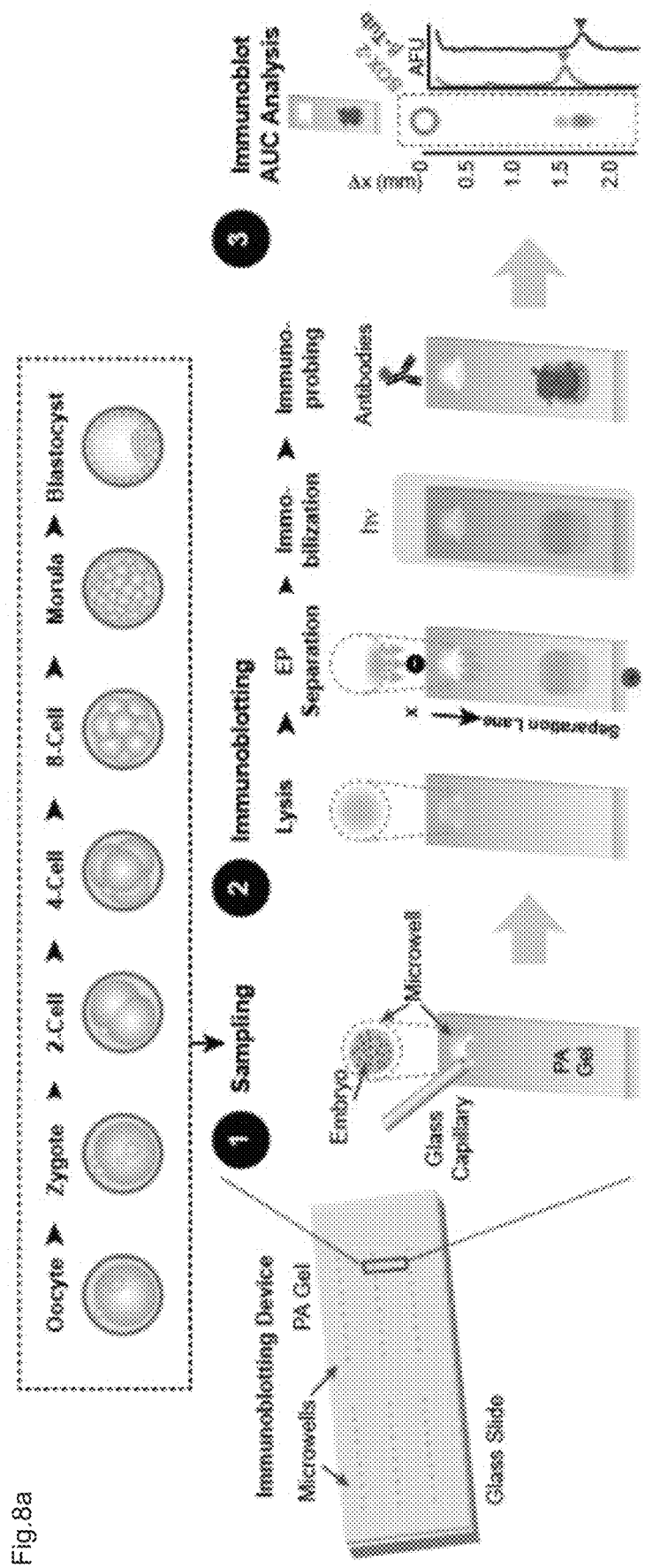

We first sought to directly measure protein expression in cells ranging from single oocytes (~80 μm in diameter) to single blastomeres from disaggregated blastocysts (<20 μm in diameter at 3.5-4.0 days post coitus, dpc) (FIG. 8a). Sample preparation of harvested murine embryos includes (i) removal of the zona *pellucida* by incubating with acidic Tyrode's solution and, if studying disaggregated blastomeres, (ii) dissociation of embryos into individual blastomeres by incubation with trypsin and Accutase®. Samples are then loaded onto the microfluidic immunoblot, comprised of a thin polyacrylamide (PA) gel layered on a glass microscope slide stippled with an array of microwells. Unlike previous single-cell approaches that rely on random settling of cells into microwells and result in occupancies that follow a Poisson distribution, here we use a standard mouth-controlled capillary tube assembly[40] to individually seat single embryos or blastomeres into microwells with extremely high precision. Once isolated in each microwell, cell samples are chemically lysed. To minimize diffusive losses during lysis, cylindrical microwells are designed to approximate the volume of our samples and thus maintain the high local protein concentrations inside cells. Thus, for each stage we designed microwells with diameters that approximate the diameter of the individual embryo or blastomere we wish to isolate (20-160 μm).

After lysis, an electric field (E=40 V/cm; 35-75 s) is applied to drive protein polyacrylamide gel electrophoresis (PAGE) in a 3 mm-long separation lane abutting each lysate-containing microwell. Proteins are immobilized to the PA gel by UV-mediated activation of benzophenone methacrylamide moieties crosslinked into the gel matrix[25,41], a process termed photo-blotting. Size-resolved immobilized protein bands are then probed using standard primary antibodies and fluorophore-conjugated secondary antibodies, yielding single-embryo or single-blastomere immunoblots. By probing for the protein loading control β-tubulin in lysate from single oocytes down to individual blastomeres from a disaggregated blastocyst (FIG. 8b), we determined a dynamic detection range spanning femtomoles ($10^{-15}$) to tens of attomoles ($10^{-17}$), with the assumed starting protein target concentration in the μM range[42].

We next scrutinized single morula (3.0 dpc) for the loading control GAPDH and two transcription factors that are key regulators of pluripotency and differentiation[43,44], SOX-2 and CDX-2. Multiplexing is granted by the four spectral channels available with our current microarray imaging system (Genepix 400A, Molecular Devices) in combination with availability of antibodies raised in four different species. With stripping and re-probing, up to nine rounds have been reported[23]. By employing a combination of (i) primary antibodies raised in different animals (goat-anti-GAPDH, rabbit-anti-SOX-2 and mouse-anti-CDX-2) and (ii) secondary antibodies conjugated to different fluorophores (donkey-anti-goat, rabbit and mouse conjugated to AlexaFluor 555, 488 and 594, respectively), the microfluidic immunoblot resolved the three targets, with molecular masses of 37, 38 and 39 kDa, from intact morula without chemical stripping and reprobing of the gel (FIG. 8c). The observed log-linear relationship between molecular mass and migration distance distinguishes target protein bands from non-specific antibody signal and demonstrates that single-morula PAGE resolves protein targets with molecular mass as close as 1-2 kDa. Scrutiny of the electromigration behavior of targets with known molecular mass showed that in a subset of cases where protein SDS denaturation in non-reducing conditions is equivalent to conventional reducing conditions, a log-linear relationship is observed for a wide molecular mass range (from 50 to 100 kDa, FIG. 16a-c).

To incorporate mRNA analysis from the same samples, we substitute the glass slide substrate of our immunoblotting device for a functionalized polyester polymer film (GelBond™ PAG Film) (FIG. 8d). Embryos sampled into microwells are treated with a fractionation lysis buffer[45] to selectively lyse the cytoplasmic compartment of the embryos. Cytoplasmic proteins are then electrophoresed and photo-blotted to the PA for subsequent immunoprobing, while nuclei are retained in the microwells. Using a $CO_2$ laser, 2 mm by 3 mm sections of the polymer film encompassing single microwells are excised from the device. These nuclei-containing device sections, or gel pallets, are processed for nucleic acid analysis. While gel pallets can be harvested for DNA, mRNA or both, here we isolated mRNA and converted it to cDNA for target pre-amplification and analysis by RT-qPCR.

To validate our ability to measure mRNA from nuclei extracted from the polymer-based immunoblotting device, we assayed single blastocysts and ran RT-qPCR analysis on mRNA isolated from gel palettes. qPCR analysis of single blastocysts shows that cycle threshold ($C_T$) values for loading control β-actin are significantly higher than negative controls, which included (i) blanks, (ii) gel pallets with empty microwells and (iii) no reverse transcriptase controls, or -RT (FIG. 8e).

Single-embryo and single-blastomere immunoblotting detects biological variation. Given our ability to immunoblot dissociated blastomeres, we next examined (i) if embryo disaggregation artificially alters the protein abundance of the whole embryo and (ii) if we can reconstruct the expression profile of the whole embryo, even when constituent blastomeres are assayed individually.

We first inquired if loading a pre-determined increase of protein in the microfluidic immunoblot would yield a concomitant increase in protein signal. We thus performed titrations where we controlled loaded protein by using individual blastomeres from dissociated four-cell embryos (2.0 dpc) as discrete and easily manipulable loads of protein. We loaded either one or two blastomeres into microwells and assayed the microwell lysate for β-tubulin (FIG. 9a). We observed an increase in β-tubulin expression (area-under-the-curve signal or AUC) from microwells loaded with two blastomeres as compared to microwells loaded with one blastomere (Mann Whitney U Test, p value=$6.28 \times 10^{-5}$, with N=7 and 11 microwells, respectively, FIG. 9a). The observation corroborates the supposition that two blastomeres would contain two-fold more protein than a single blastomere.

We next sought to assess if the protein profile of a whole embryo could be reconstructed from immunoblots of individual, dissociated blastomeres, to rule out the concern of material loss during disaggregation, lysis or electrophoresis. To do so, we simultaneously assayed (i) intact four-cell embryos and (ii) blastomeres from disaggregated four-cell embryo (each blastomere contained in a separate microwell) (FIG. 9b). We observed that protein bands for whole embryos had larger sample dispersion than protein bands for dissociated blastomeres. We attribute the larger sample dispersion from whole embryos to the 4-fold larger starting sample mass than in dissociated blastomeres. All protein peaks passed the quality control metrics of (i) signal-to-noise (SNR) ratios above the threshold of 3 and (ii) Gaussian fit with $R^2>0.8$. (FIG. 9b).

The resulting AUCs for β-tubulin were normalized to the summed immunoblot signal from the four disaggregated blastomeres (FIG. 9b). While the inter-embryonic variation showed an average embryo-to-embryo variation in total β-tubulin of 8%, we observed no significant difference between the sum of the contributions of dissociated blastomeres and signal obtained from a four-cell embryo (Wilcoxon matched-pairs signed rank test, p value=0.5, N=3 independent experiments) (FIG. 9b). We observed similar results with additional protein markers β-actin and GADD45a (FIG. 18). These results indicate that immunoblotting of individual blastomeres can reconstruct the protein profile of the originating intact four-cell embryo.

Finally, we sought to assess if the source of the observed inter-blastomeric variation in β-tubulin AUC was attributable to biological variation or confounding technical variation. First, we established a technical variation threshold by quantifying immunoblots of microwells uniformly loaded with purified protein. Given that endogenous loading control protein targets (i) show significant cell-to-cell variation[46,47] or (ii) form dimers that are difficult to solubilize[48], we utilize purified protein to estimate technical variation as we have previously reported[19]. Briefly, we partitioned a solution of purified bovine serum albumin (BSA, 1 μM in PBS) into the microwells by incubating PA gels in BSA solution for 30 min. We then performed the immunoblotting assay and quantified BSA protein band AUC. We calculated the coefficient of variation in BSA AUC ($CV_{AUC}$ %=AUC standard deviation (S.D.)/mean AUC×100) and computed a technical variation threshold defined as >3×S.D. of the mean $CV_{AUC}$[49] ($CV_{threshold}$=mean $CV_{AUC}$+3 S.D.=7.4%, where mean $CV_{AUC}$=4.69% and S.D.=0.92%, FIG. 14a-b). For all dissociated four-cell embryos studied, the inter-blastomeric β-tubulin expression CV exceeded the technical variation threshold ($CV_S$=8.3%, 19.6% and 11.3% for embryos, FIG. 9b). Consequently, we attribute the inter-blastomeric variation to biological variation and not technical variation.

Single-blastomere immunoblotting allows for normalization of marker expression by loading controls. We next tested whether the widely-used loading controls β-tubulin and β-actin are accurate indicators of cell volume in preimplantation embryos. Normalization of protein expression by a loading control that is strongly correlated with cell size is crucial for elucidating true phenotypic differences between cells, as cellular concentration is a more accurate indicator of cell phenotype than total abundance[50,51]. However, at the mRNA level commonly employed housekeeping genes (e.g., β-actin and β-tubulin) are not stably and homogeneously expressed across different samples, experimental conditions or treatments[52]. To study if this variability prevails at the protein level, we assayed dissociated morula blastomeres for β-tubulin and ß-actin and compared protein expression (AUC) to cell volume (computed from brightfield images of cells seated in microwells) (FIG. 10a). We observed a significant, positive correlation between cell volume and protein expression of both β-tubulin and β-actin (FIG. 10b) indicating that at the protein level, both β-tubulin and β-actin serves as an adequate loading controls for blastomere and embryo-scale immunoblotting.

We further tested β-tubulin and β-actin as loading controls by immunoblotting the same dissociated morula blastomeres for SOX-2 and normalizing SOX-2 expression by expression either β-tubulin or β-actin. We observed an expected negative correlation[53,54] between normalized SOX-2 expression and volume of morula blastomeres for both β-tubulin and β-actin (FIG. 10b). This negative correlation between cell volume and SOX-2 expression became significant at the blastocyst stage, where blastomeres have fully differentiated into either inner cell mass (ICM) or trophectoderm (TE)[54] (FIG. 17).

Indexing endpoint immunoblot results with micrographs of the originating and intact cell sample allows us to determine whether loading controls are correlated with cell volume. Once this correlation has been determined, multiplexing capabilities allow for normalization of targets by loading controls, such as β-tubulin, even if information on cell volume is not available.

Microfluidic immunoblotting detects truncated DICER-1 isoform expression in oocytes and two-cell embryos. Alternative splicing is frequent during early embryonic development in mouse and human[55-57]. However, efforts to investigate whether the corresponding alternate protein isoforms are ultimately and stably generated require pooling tens of thousands of collected embryos from each stage, losing intra-blastomeric information in the process[58]. Thus, resolving proteoforms generated by alternative splicing demands tools with single-embryo and single-blastomere resolution.

To this end, we aimed to examine one of the earliest known examples of a protein isoform that exists in mouse development. DICER-1 is essential for small RNA-mediated gene expression regulation. By processing small RNAs into their mature form, DICER-1 generates the sequence-specific guides required by effector complexes to target cognate mRNAs and repress their translation[59]. Bulk analyses of mouse oocytes found high expression of an N-terminally truncated isoform, denoted DICER$^O$ [59] (FIG. 11a). DICER$^O$ demonstrates higher catalytic activity than its full-length form and is believed to drive the high activity of endogenous small interfering RNAs (endo-siRNAs) in mouse oocytes, but not in somatic cells[59]. The Dicer$^O$ transcript persists until the fertilized zygote stage.

To explore whether DICER$^O$ is specific to the oocyte stage, we assayed oocytes and two-cell embryos for isoforms of DICER-1. We collected oocytes and two-cell embryos and divided each sample for analysis of either protein by microfluidic immunoblotting or mRNA analysis by single-embryo quantitative reverse transcription polymerase chain reaction (qRT-PCR) (FIG. 11b). Despite a lack of an isoform-specific antibody, PAGE resolved multiple DICER-1 isoforms by molecular mass. We observed that both oocytes and two-cell embryos expressed isoforms of DICER-1 (FIG. 11c). Sample preparation for single-embryo PAGE is not equivalent to sample preparation in bulk, slab-gel SDS-PAGE. Specifically, single-embryo PAGE uses non-reducing conditions and, perhaps most importantly, a dual-functionality and rapid (60-70 sec) lysis and protein solubilization step. Consequently, we do not expect equivalent protein sizing for all targets in the single cell versus bulk assay. That said, given the retained relative order of electromigration, we assign the highest molecular mass band as the full-length DICER-1 form and the lower molecular mass band as the truncated isoform (FIG. 15a-c).

For oocytes, we observed significantly higher expression of the truncated isoform over the full-length DICER-1 for both mRNA (normalized by endogenous control Rfx1) and protein (AUC) (FIG. 11d). On the other hand, we found no significant difference between expression of truncated and full-length isoforms of DICER-1 in two-cell embryos (FIG. 11d).

When comparing expression levels between embryonic stages, we observed that for both mRNA and protein the expression, full-length DICER-1 expression was not significantly different between oocytes and two-cell embryos (FIG. 11d). For the truncated isoform, however, we observed a significant decrease in both mRNA levels and protein levels from the oocyte to the two-cell stage (FIG. 11d). Hence, protein PAGE from single-embryo lysates grants the selectivity required for measuring protein isoforms, even when pan-specific antibodies are the only reagent available.

Single-blastomere immunoblotting reports GADD45a expression heterogeneity in two- and four-cell embryos. We next sought to inspect early-stage embryos for lineage biases by measuring protein expression from disaggregated two-cell and four-cell embryos. The exact stage and circumstances by which blastomeres first acquire certain fates remains unknown. On the one hand, it is thought that embryonic plasticity supports blastomere symmetry up to the 8-cell embryo, where embryos can compensate for the loss of one blastomere as early as the two-cell stage[60]. On the other hand, studies showing consistent bimodal expression of genes related to differentiation in sister blastomeres suggests that the involved factors may not be inherited equally by all blastomeres[14]. Whether or not this heterogeneity is transcriptional noise or leads to functional heterogeneity in the subsequent protein products remains an open question.

As such, to quantitatively examine intra-embryonic heterogeneity in cell fate related markers, we assayed early-stage blastomeres for GADD45a, a protein involved in DNA damage repair that has been reported to show bimodal transcription at the two-cell and four-cell stages[4] (FIG. 12a). We compared the intra-embryonic heterogeneity of GADD45a expression to that of loading controls β-tubulin and β-actin, to control for stochasticity of protein partitioning at cell division[61]. We observed that the intra-embryonic variation in GADD45a expression is significantly higher than the variation in both β-actin and β-tubulin expression (FIGS. 12b & 12c). Furthermore, normalization by β-tubulin expression did not decrease the GADD45a CVs. These findings indicate that blastomeres of four-cell embryos show heterogeneous expression of GADD45a, in agreement with previous mRNA and IF-based findings[4].

We next investigated if heterogeneity in GADD45a expression arises in the earlier two-cell embryo. Unlike in the four-cell stage, bimodality in GADD45a protein expression at the two-cell stage remains unexplored. We thus assayed dissociated two-cell embryos to understand the intra-embryonic distribution of GADD45a. To test whether one blastomere consistently showed higher GADD45a AUC than the other, we immunoblotted dissociated two-cell blastomeres for GADD45a and loading controls β-tubulin and β-actin (FIG. 12d) and computed the $CV_{expression}$ between blastomeres for the three protein markers (FIG. 12e). Unlike for the four-cell embryos, the increase in CV for GADD45a expression over β-tubulin and β-actin was not statistically significant (FIG. 12f). Thus, while the expression of GADD45a at the four-cell stage shows higher heterogeneity than both markers that serve as reliable proxies of cell volume, the same cannot be said about the two-cell sister blastomeres.

Given the unique nature of two-cell embryo, which is the only "multicellular" stage of development undergoing both zygotic genome activation and maternal clearance[62], the levels of protein and mRNA are unsurprisingly unstable and preclude development of a reliable normalization metric. While the exact nature of the transcriptional, translational and degradation events occurring within the two cell embryos are not completely clear at this time, our single embryo western approach provides a means to further explore these biological processes in the unique two-cell state.

Correlation between mRNA and protein changes from the two- and four-cell embryo to the morula stage. We finally sought to investigate whether differences in correlation between protein and mRNA could be detected between early stage embryos (two- and four-cell) where transcripts are maternally inherited and late stages (morula and blastocyst) where instead the zygotic genome is activated and maternal transcripts are largely cleared by active and passive mechanisms[62,63].

We performed same-embryo mRNA and immunoblotting assays on two-cell, four-cell embryos and morula/blastocysts and measured protein and mRNA expression of the loading control β-actin. We first compared β-actin CT values to negative controls (laser-excised device pallets containing empty microwells, reaction without RT enzyme, or no template controls). We found that for two-cell and four-cell and embryos, negative controls did not amplify (FIG. 13b). For blastocysts, the β-actin CT values were significantly higher than the various negative controls (FIG. 13b).

We finally studied the correlation between protein and mRNA expression of β-actin. Interestingly, for two and four-cell embryos we found the positive correlation between b-actin protein expression and b-actin $C_T$, and thus negative correlation between protein expression and mRNA expression, to be non-significant. This result is in line with the transitioning status of the embryo from maternally deposited transcripts and proteins are being actively and passively degraded at different rates, to the more stable environment of the post zygotically activated blastocyst, at which point maternal clearance is largely or totally complete[63,64]. In support of this, at the morula and blastocyst stages, β-actin C and protein expression showed a significant, negative correlation, indicating that the expression of mRNA and protein are positively correlated.

Our microfluidic design provides an avenue for a cellular-resolution in the form of protein immunoblotting applicable to mammalian development as early as the oocyte stage of a murine model.

As detailed here, the ~10-20 embryos harvested from a single mouse donor are sufficient not just for one immunoblot, but for multiple single-embryo and single-blastomere immunoblots. The precision in sample handling and in enhanced sensitivity notably reduces the conventional PAGE sample requirements of several hundreds or thousands of embryos[58,59]. The implications are multi-fold. First, as single-embryo immunoblots inherently and dramatically lower sample requirements, the burden of animal sacrifice is likewise reduced. Current gold-standard protein measurements consist of conventional western blotting, which depending on expected protein abundance, require combination of 50-100 embryos to ensure a detectable signal[69]. These issues are made further dismal in cases involving subfertility or when a specific genotype is required. For wild type mouse conditions, this would require the sacrifice of 5-10 mice per lane (or measurement). If a specific genotype is needed, then this value is multiplied by the difficulty in procuring the needed samples. With the strategy described here, a single mouse can provide sufficient material for up 10-20 individual measurements. Second, statistical interpretation of single-embryo and single-blastomere immunoblot results is feasible, revealing intra-embryonic heterogeneity, as well as significant differences between embryos of the same fertilization event and between donors. Finally, immunoblots can be stored and re-probed for additional proteins as novel, important targets emerge in the rapidly advancing field of developmental biology.

Lastly, we simultaneously immunoblot and measure mRNA from embryos of the same donor, thus enhancing the biological accuracy of correlations between mRNA levels and protein expression at different stages of the preimplantation embryo. Such insight into the expression dynamics would clarify how modulation in transcription dictates cellular phenotype[70]. Indeed, our finding more accurately characterize the discrepancy between transcript abundance and protein presence in the early pre-implantation embryo, a phenomenon that is ameliorated by the morula and blastocysts stages, which coincides precisely with the maternal to zygotic transition experienced by all preimplantation embryos of every species. Moreover, with the advent of new gene editing technologies, (e.g., CRISPR, genomic screening methods including targeted, exome or whole genome sequencing) screening for on-target and off-target activity has become critical, as unintended editing events can lead to exon skipping, alternative splicing and deletions that occasionally lead to active versions of supposedly "knocked out" targets[71-74]. Protein assays that can complement genomic screening, such as described here will be crucial for screening embryos for protein-level effects of both on-target and off-target mutations, even when the latter occur in non-coding regions.

Device Fabrication. Devices for protein immunoblotting were fabricated on silanized glass slides using microposts patterned on SU-8 wafers to mold the PA gel microwells, as previously reported[41]. Diameter and height of the microwells was optimized for each sample. Microwell diameter and height was optimized for each sample, where microwell diameter approximates the average blastomere or embryo diameter (from 20 μm for dissociated blastocyst blastomeres to 150 μm for whole embryos) and the diameter-to-height ratio was kept at approximately 3:4 to prevent convection streamlines from dislodging settled cells during the pouring of lysis buffer[23]. In devices for same-embryo immunoblotting and mRNA measurements, microwell diameter and height were 200 μm, in order to allow alignment of laser over the area containing the microwells.

Polyacrylamide precursor solution including acrylamide/bis-acrylamide (7-12% T) and 3 mM BPMAC was degassed with sonication for 9 min. 0.08% APS and 0.08% TEMED were added to precursor solution and solution was pipetted between the SU-8 wafer (rendered hydrophobic with Gel Slick™ solution) and either (i) a glass microscope slide functionalized with 3-(trimethoxylsilyl)propyl methacrylate (to ensure covalent grafting of PA gel to glass surface) for standard immunoblotting, or (ii) GelBond™ polymer cut to the size of a standard glass slide for same-embryo immunoblotting and mRNA measurements. After chemical polymerization (20 min), devices (glass with grafted PA gel layer) were lifted from wafer, rinsed with deionized water and stored dry until use.

REFERENCES

1. Motosugi, et al. Polarity of the mouse embryo is established at blastocyst and is not prepatterned. *Genes Dev.* 19, 1081-1092 (2005).

2. Alarcon, V. B. & Marikawa, Y. Unbiased Contribution of the First Two Blastomeres to Mouse Blastocyst Development. *Mol. Reprod. Dev.* 72, 354-361 (2005).
3. Fujimori, T., Kurotaki, Y., Miyazaki, J. & Nabeshima, Y. Analysis of cell lineage in two- and four-cell mouse embryos. *Development* 130, 5113-5122 (2003).
4. Biase, F. H., Cao, X. & Zhong, S. Cell fate inclination within 2-cell and 4-cell mouse embryos revealed by single-cell RNA sequencing. *Genome Res.* 24, 1787-1796 (2014).
5. Xue, Z. et al. Genetic programs in human and mouse early embryos revealed by single-cell RNA sequencing. *Nature* 500, 593-597 (2013).
6. Torres-Padilla, M. E., Parfitt, D. E., Kouzarides, T. & Zernicka-Goetz, M. Histone arginine methylation regulates pluripotency in the early mouse embryo. *Nature* 445, 214-218 (2007).
7. Goolam, M. et al. Heterogeneity in Oct4 and Sox2 Targets Biases Cell Fate in 4-Cell Mouse Embryos. *Cell* 165, 61-74 (2016).
8. White, M. D. et al. Long-Lived Binding of Sox2 to DNA Predicts Cell Fate in the Four-Cell Mouse Embryo. *Cell* 165, 75-87 (2016).
9. Plachta, N., et al. Oct4 kinetics predict cell lineage patterning in the early mammalian embryo. *Nat. Cell Biol.* 13, 117-123 (2011).
10. Shi, J. et al. Dynamic transcriptional symmetry-breaking in pre-implantation mammalian embryo development revealed by single-cell RNA-seq. *Development* 142, 3468-3477 (2015).
11. Bischoff, M., Parfitt, D.-E. & Zernicka-Goetz, M. Formation of the embryonic-abembryonic axis of the mouse blastocyst: relationships between orientation of early cleavage divisions and pattern of symmetric/asymmetric divisions. *Development* 135, 953-962 (2008).
12. Piotrowska-Nitsche, K. & Zernicka-Goetz, M. Spatial arrangement of individual 4-cell stage blastomeres and the order in which they are generated correlate with blastocyst pattern in the mouse embryo. *Mech. Dev.* 122, 487-500 (2005).
13. Zheng, Z., Li, H., Zhang, Q., Yang, L. & Qi, H. Unequal distribution of 16S mtrRNA at the 2-cell stage regulates cell lineage allocations in mouse embryos. *Reproduction* 151, 351-367 (2016).
14. Casser, E. et al. Totipotency segregates between the sister blastomeres of two-cell stage mouse embryos. *Sci. Rep.* 7, 1-15 (2017).
15. Bordeaux, J. et al. Antibody validation. *Biotechniques* 48, 197-209 (2010).
16. Trenchevska, O., Nelson, R. W. & Nedelkov, D. Mass spectrometric immunoassays for discovery, screening and quantification of clinically relevant proteoforms. *Bioanalysis* 8, 1623-1633 (2016).
17. Schnell, U., Dijk, F., Sjollema, K. A. & Giepmans, B. N. G Immunolabeling artifacts and the need for live-cell imaging. *Nat. Methods* 9, 152-158 (2012).
18. Teves, S. S. et al. A dynamic mode of mitotic bookmarking by transcription factors. *Elife* 5, 1-24 (2016).
19. Zhu, Y. et al. Nanodroplet processing platform for deep and quantitative proteome profiling of 10-100 mammalian cells. *Nat. Commun.* DOI: 10.1038/s41467-018-03367-w (2018). doi: 10.1038/s41467-018-03367-w
20. Zhu, Y. et al. Proteomic Analysis of Single Mammalian Cells Enabled by Microfluidic Nanodroplet Sample Preparation and Ultrasensitive NanoLC-MS. *Angew. Chemie Int. Ed.* 14642, 12370-12374 (2018).
21. Budnik, B., Levy, E. & Slavov, N. Mass-spectrometry of single mammalian cells quantifies proteome heterogeneity during cell differentiation. *biorXiv* 1-16 (2017). doi: 10.1101/102681
22. Specht, H. & Slavov, N. Transformative Opportunities for Single-*Cell* Proteomics. *J Proteome Res.* 17, 2562-2571 (2018).
23. Hughes, A. J. et al. Single-cell western blotting. *Nat. Methods* 11, 749-55 (2014).
24. Kang, C.-C. et al. Single cell-resolution western blotting. *Nat. Protoc.* 11, 1508-1530 (2016).
25. Kang, C. C., Lin, J. M. G., Xu, Z., Kumar, S. & Herr, A. E. Single-cell western blotting after whole-cell imaging to assess cancer chemotherapeutic response. *Anal. Chem.* 86, 10429-10436 (2014).
26. Kim, J. J., Sinkala, E. & Herr, A. E. High-selectivity cytology via lab-on-a-disc western blotting of individual cells. *Lab Chip* 17, 855-863 (2017).
27. Yao, X. et al. Functional analysis of single cells identifies a rare subset of circulating tumor cells with malignant traits. *Integr. Biol. (Camb).* 6, 388-98 (2014).
28. Yamauchi, K. A. & Herr, A. E. Subcellular western blotting of single cells. *Microsystems Nanoeng.* 3, 16079 (2017).
29. Tsichlaki, E. & Fitzharris, G. Nucleus downscaling in mouse embryos is regulated by cooperative developmental and geometric programs. *Sci. Rep.* 6, 1-7 (2016).
30. Epifano, O., et al. Coordinate expression of the three zona *pellucida* genes during mouse oogenesis. *Development* 121, 1947-1956 (1995).
31. Martín-Coello, et a. Superovulation and in vitro oocyte maturation in three species of mice. *Theriogenology* 70, 1004-1013 (2008).
32. Marangos, P. in *Oogenesis: Methods and Protocols* (ed. Nezis, I. P.) 209-215 (Springer New York, 2016). doi: 10.1007/978-1-4939-3795-0_15
33. Tang, F. et al. RNA-Seq analysis to capture the transcriptome landscape of a single cell. *Nat. Protoc.* 5, 516-535 (2010).
34. Darmanis, S. et al. Simultaneous Multiplexed Measurement of RNA and Proteins in Single Cells. *Cell Rep.* 14, 380-389 (2016).
35. Nicolet, et al Combined Single-*Cell* Measurement of Cytokine mRNA and Protein Identifies T Cells with Persistent Effector Function. *J. Immunol.* 198, 962-970 (2017).
36. Eliscovich, C., Shenoy, S. & Singer, R. Imaging mRNA and protein interactions within neurons. *Proc. Natl. Acad. Sci.* 114, E1875-E1884 (2017).
37. Frei, A. et al. Highly multiplexed simultaneous detection of RNAs and proteins in single cells. *Nat Methods* 3, (2016).
38. Peterson, V. et al. Multiplexed quantification of proteins and transcripts in single cells. *Nat Biotechnol* 35, 936-939 (2017).
39. Zabzdyr, J. L. & Lillard, S. J. Electrophoretic Profiling of Both RNA and Protein from a Single 250-pL Sample. *Anal. Chem.* 74, 1857-1862 (2002).
40. Chen, S., et al. Highly efficient mouse genome editing by CRISPR ribonucleoprotein electroporation of zygotes. *J. Biol. Chem.* 291, 14457-14467 (2016).
41. Hughes, A. J., Lin, R. K. C., Peehl, D. M. & Herr, A. E. Microfluidic integration for automated targeted proteomic assays. *Proc. Natl. Acad. Sci.* U.S.A 109, 5972-7 (2012).
42. Mozziconacci, J., et al. Tubulin dimers oligomerize before their incorporation into microtubules. *PLoS One* 3, 1-8 (2008).

43. Strumpf, D. et al. Cdx2 is required for correct cell fate specification and differentiation of trophectoderm in the mouse blastocyst. *Development* 132, 2093-2102 (2005).
44. Zhang, S. Sox2, a key factor in the regulation of pluripotency and neural differentiation. *World J. Stem Cells* 6, 305 (2014).
45. Yamauchi, K. A. & Herr, A. E. Subcellular western blotting of single cells. *Microsystems Nanoeng.* 3, 16079 (2017).
46. Eaton, S. L. et al. Total Protein Analysis as a Reliable Loading Control for Quantitative Fluorescent Western Blotting. *PLoS One* 8, e72457 (2013).
47. Li, R. & Shen, Y. An old method facing a new challenge: re-visiting housekeeping proteins as internal reference control for neuroscience research. *Life Sci* 92, 747-751 (2013).
48. Qvit, N., et al. Glyceraldehyde-3-Phosphate Dehydrogenase (GAPDH) Protein-Protein Interaction Inhibitor Reveals a Non-catalytic Role for GAPDH Oligomerization in *Cell* Death *. 291, 13608-13621 (2016).
49. Sinkala, E. et al. Profiling protein expression in circulating tumour cells using microfluidic western blotting. *Nat. Commun.* 8, (2017).
50. Padovan-Merhar, O. et al. Single Mammalian Cells Compensate for Differences in Cellular Volume and DNA Copy Number through Independent Global Transcriptional Mechanisms. *Mol. Cell* 58, 339-352 (2015).
51. Kempea, H., Schwabeb, A., Crémazya, F., Verschurea, P. J. & Bruggemanb, F. J. The volumes and transcript counts of single cells reveal concentration homeostasis and capture biological noise. *Mol. Biol. Cell* 26, 797-804 (2015).
52. Jeong, J.-K. et al. Evaluation of reference genes in mouse preimplantation embryos for gene expression studies using real-time quantitative RT-PCR (RT-qPCR). *BMC Res. Notes* 7, 675 (2014).
53. Wicklow, E. et al. HIPPO Pathway Members Restrict SOX2 to the Inner *Cell* Mass Where It Promotes ICM Fates in the Mouse Blastocyst. *PLoS Genet.* 10, (2014).
54. Ziomek, C. A., Johnson, M. H. & Handyside, A. H. The developmental potential of mouse 16-cell blastomeres. *J. Exp. Zool.* 221, (1982).
55. Revil, T., Gaffney, D., Dias, C., Majewski, J. & Jerome-Majewska, L. A. Alternative splicing is frequent during early embryonic development in mouse. *BMC Genomics* 11, 399 (2010).
56. Pan, Q., et a. Deep surveying of alternative splicing complexity in the human transcriptome by high-throughput sequencing. *Nat. Genet.* 40, 1413-1415 (2008).
57. Wang, E. T. et al. Alternative isoform regulation in human tissue transcriptomes. *Nature* 456, 470-476 (2008).
58. Gao, Y. et al. Protein Expression Landscape of Mouse Embryos during Pre-implantation Development. *Cell Rep.* 21, 3957-3969 (2017).
59. Flemr, M. et al. A retrotransposon-driven dicer isoform directs endogenous small interfering rna production in mouse oocytes. *Cell* 155, 807-816 (2013).
60. Morris, S. A., Guo, Y. & Zernicka-Goetz, M. Developmental Plasticity Is Bound by Pluripotency and the Fgf and Wnt Signaling Pathways. *Cell Rep.* 2, 756-765 (2012).
61. Huh, D. & Paulsson, J. Random partitioning of molecules at cell division. *Proc. Natl. Acad. Sci.* 108, 15004-15009 (2011).
62. Lee, M. T., Bonneau1, A. R. & Giraldez, A. J. Zygotic genome activation during the maternal-to-zygotic transition. *Annu Rev Cell Dev Biol* 30, 581-613 (2014).
63. Tadros, W. & Lipshitz, H. D. The maternal-to-zygotic transition: a play in two acts. *Development* 136, 3033-3042 (2009).
64. Hamatani, T., et al. Dynamics of Global Gene Expression Changes during Mouse Preimplantation Development. *Dev. Cell* 6, 117-131 (2004).
65. Schultz, R. M. Regulation of zygotic gene activation in the mouse. *BioEssays* 15, 531-538 (1993).
66. Nothias, J. Y., Miranda, M. & DePamphilis, M. L. Uncoupling of transcription and translation during zygotic gene activation in the mouse. *EMBO J.* 15, 5715-25 (1996).
67. Schwanhausser, B. et al. Corrigendum: Global quantification of mammalian gene expression control. *Nature* 495, 126-127 (2013).
68. Snider, N. T. & Omary, M. B. Post-translational modifications of intermediate filament proteins: Mechanisms and functions. *Nat. Rev. Mol. Cell Biol.* 15, 163-177 (2014).
69. Zhang, J. Y., Diao, Y. F., Kim, H. R. & Jin, D. Il. Inhibition of Endoplasmic Reticulum Stress Improves Mouse Embryo Development. s7, e40433 (2012).
70. Macaulay, I. C., Ponting, C. P. & Voet, T. Single-*Cell* Multiomics: Multiple Measurements from Single Cells. *Trends Genet.* 33, 155-168 (2017).
71. Zischewski, J., et al. Detection of on-target and off-target mutations generated by CRISPR/Cas9 and other sequence-specific nucleases. *Biotechnol. Adv.* 35, 95-104 (2017).
72. Shigeru Makino, et al. Illegitimate translation causes unexpected gene expression from on-target out-of-frame alleles created by CRISPR-Cas9. *Sci. Rep.* 6, 39608 (2016).
73. Lee, H. & Jin-Soo Kim. Unexpected CRISPR on-target effects. *Nat. Biotechnol.* 36, 703-704 (2018).
74. Chen, D. et al. CRISPR/Cas9-mediated genome editing induces exon skipping by complete or stochastic altering splicing in the migratory locust. *BMC Biotechnol.* 18, (2018).
75. Santa Cruz Biotechnologies. Dicer Antibody (A-2): sc-136981. (2019). Available at: https://www.scbt.com/scbt/product/dicer-antibody-a-2.
76. Que, J. et al. Multiple dose-dependent roles for Sox2 in the patterning and differentiation of anterior foregut endoderm. *Development* 134, 2521-2531 (2007).
77. Abcam. Anti-GADD45A antibody (ab180768). (2019). Available at: https://www.abcam.com/gadd45a-antibody-ab180768.html.
78. Johnson, D. E., Ostrowski, P., Jaumouillé, V. & Grinstein, S. The position of lysosomes within the cell determines their luminal pH. *J. Cell Biol.* 212, 677-692 (2016).

Unless contraindicated or noted otherwise, in these descriptions and throughout this specification, the terms "a" and "an" mean one or more, the term "or" means and/or. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

The invention claimed is:

1. A polyacrylamide gel-based device that integrates electrophoretic separation of cytoplasmic proteins and extraction of nucleic acids from nuclei, the device comprising a polyacrylamide gel covalently grafted to a polyester film, wherein the gel comprises microwells and corresponding separation lanes, wherein each microwell contains fractionated nuclei of cells, and each corresponding separation lane comprises electrophoretically separated proteins of the cells.

2. The device of claim 1, wherein each microwell abuts the corresponding separation lane.

3. The device of claim 1, wherein each microwell is contained in an excised gel raft, wherein a void created by excision of the gel raft abuts the corresponding separation lane.

4. The device of claim 1, wherein each microwell is contained in an excised gel raft, wherein a void created by excision of the gel raft abuts the corresponding separation lane, and each gel raft is contained in a reaction vessel wherein nucleic acid from then nuclei is extracted.

5. The device of claim 1, wherein the proteins are photocaptured by UV-light activated benzophenone moieties incorporated in the gel.

6. The device of claim 1 wherein the gel is 100-150 µm-thick, and the microwells are cylindrical of diameters of 20-160 µm.

7. The device of claim 1 wherein each microwell contains fractionated nuclei of 1-100 cells.

8. The device of claim 1 wherein each microwell contains fractionated nuclei of 10-100 cells.

9. The device of claim 1, further comprising a membrane comprising a transverse electrophoretic protein blot of the gel.

10. The device of claim 1 wherein each microwell contains fractionated nuclei of cells, wherein the cells are of a biopsy.

11. The device of claim 1 wherein each microwell contains fractionated nuclei of cells, wherein the cells are of a single embryo or single blastomere.

12. The device of claim 2 wherein each microwell contains fractionated nuclei of cells, wherein the cells are of a single embryo or single blastomere.

13. The device of claim 3 wherein each microwell contains fractionated nuclei of cells, wherein the cells are of a single embryo or single blastomere.

14. The device of claim 4 wherein each microwell contains fractionated nuclei of cells, wherein the cells are of a single embryo or single blastomere.

15. The device of claim 5 wherein each microwell contains fractionated nuclei of cells, wherein the cells are of a single embryo or single blastomere.

16. The device of claim 6 wherein each microwell contains fractionated nuclei of cells, wherein the cells are of a single embryo or single blastomere.

17. The device of claim 7 wherein each microwell contains fractionated nuclei of cells, wherein the cells are of a single embryo or single blastomere.

18. The device of claim 8 wherein each microwell contains fractionated nuclei of cells, wherein the cells are of a single embryo or single blastomere.

19. The device of claim 9 wherein each microwell contains fractionated nuclei of cells, wherein the cells are of a single embryo or single blastomere.

20. A method integrating electrophoretic separation of cytoplasmic proteins and extraction of nucleic acids from nuclei using the device of claim 1, the method comprising
performing on the contained nuclei a genomic or transcriptomic measurement; and
performing on the separated proteins a protein measurement.

* * * * *